US009545507B2

(12) United States Patent
Ross

(10) Patent No.: US 9,545,507 B2
(45) Date of Patent: *Jan. 17, 2017

(54) INJECTION MOLDED MICRONEEDLE ARRAY AND METHOD FOR FORMING THE MICRONEEDLE ARRAY

(75) Inventor: Russell Frederick Ross, Atlanta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 438 days.

This patent is subject to a terminal disclaimer.

(21) Appl. No.: 13/641,507

(22) PCT Filed: Apr. 27, 2011

(86) PCT No.: PCT/IB2011/051860
§ 371 (c)(1),
(2), (4) Date: Feb. 22, 2013

(87) PCT Pub. No.: WO2012/020332
PCT Pub. Date: Feb. 16, 2012

(65) Prior Publication Data
US 2013/0144217 A1 Jun. 6, 2013

Related U.S. Application Data

(60) Provisional application No. 61/328,723, filed on Apr. 28, 2010, provisional application No. 61/411,071, (Continued)

(51) Int. Cl.
*A61M 37/00* (2006.01)
*A61B 17/20* (2006.01)
(Continued)

(52) U.S. Cl.
CPC ........ *A61M 37/0015* (2013.01); *A61B 17/205* (2013.01); *A61K 38/191* (2013.01);
(Continued)

(58) Field of Classification Search
CPC ............... A61M 37/0015; A61M 2037/003; A61M 2037/0023; A61M 2037/0038; A61M 2037/0046; A61M 2037/0056; A61M 2037/0061; A61M 2037/0053; A61K 9/0021; A61K 9/703; A61K 38/191; A61B 17/205; Y10T 156/1057; Y10T 156/10; Y10T 156/1039
See application file for complete search history.

(56) References Cited

U.S. PATENT DOCUMENTS 3,797,494 A 3/1974 Zaffaroni
3,964,482 A 6/1976 Gerstel et al.
(Continued)

FOREIGN PATENT DOCUMENTS

EP 2 100 850 9/2009
EP 2100820 A1 9/2009
(Continued)

OTHER PUBLICATIONS

Ahmed et al; "Bis(diacetylene)s I: Langmuir-Blodgett films", Thin Solid Films 187: 141-153; 1990.
(Continued)

*Primary Examiner* — Theodore Stigell
*Assistant Examiner* — Amber Stiles
(74) *Attorney, Agent, or Firm* — Dority & Manning, P.A.

(57) ABSTRACT

Disclosed are injection molded devices including microneedles on a substrate base. The microneedles may include a plurality of nano-sized structures fabricated thereon. The molds used to form the microneedles are assembled from a plurality of mold segments, each defining portions of the microneedles. Upon assembly of the multiple mold segments, microneedle negative cavities are formed. The molds may be used in an injection molding process to
(Continued)

form microneedle arrays. Devices may be utilized for interacting with a component of the dermal connective tissue.

26 Claims, 21 Drawing Sheets

Related U.S. Application Data filed on Nov. 8, 2010, provisional application No. 61/435,939, filed on Jan. 25, 2011.

(51) Int. Cl.
*A61K 38/19* (2006.01)
*A61K 9/00* (2006.01)

(52) U.S. Cl.
CPC ...... *A61K 9/0021* (2013.01); *A61M 2037/003* (2013.01); *A61M 2037/0023* (2013.01); *A61M 2037/0053* (2013.01); *A61M 2037/0061* (2013.01); *Y10T 156/10* (2015.01); *Y10T 156/1039* (2015.01); *Y10T 156/1057* (2015.01)

(56) References Cited

U.S. PATENT DOCUMENTS

| | | |
|---|---|---|
| 4,031,894 A | 6/1977 | Urquhart et al. |
| 4,051,840 A | 10/1977 | Kantrowitz et al. |
| 4,201,211 A | 5/1980 | Chandrasekaran et al. |
| 4,379,454 A | 4/1983 | Campbell et al. |
| 4,436,741 A | 3/1984 | Urquhart et al. |
| 4,489,033 A | 12/1984 | Uda et al. |
| 4,515,543 A | 5/1985 | Hamner |
| 4,588,580 A | 5/1986 | Gale et al. |
| 4,615,699 A | 10/1986 | Gale et al. |
| 4,661,105 A | 4/1987 | Gale |
| 4,681,584 A | 7/1987 | Gale et al. |
| 4,698,062 A * | 10/1987 | Gale ............... A61M 35/00 424/449 |
| 4,725,272 A | 2/1988 | Gale |
| 4,832,953 A | 5/1989 | Campbell et al. |
| 4,880,633 A | 11/1989 | Loper et al. |
| 4,908,027 A | 3/1990 | Enscore et al. |
| 5,004,610 A | 4/1991 | Osborne et al. |
| 5,310,559 A | 5/1994 | Shah et al. |
| 5,328,470 A | 7/1994 | Nabel et al. |
| 5,342,623 A | 8/1994 | Enscore et al. |
| 5,344,656 A | 9/1994 | Enscore et al. |
| 5,364,630 A | 11/1994 | Osborne et al. |
| 6,132,755 A | 10/2000 | Eicher et al. |
| 6,248,281 B1 | 6/2001 | Abe et al. |
| 6,312,612 B1 | 11/2001 | Sherman et al. |
| 6,334,856 B1 | 1/2002 | Allen et al. |
| 6,375,978 B1 | 4/2002 | Kleiner et al. |
| 6,471,993 B1 | 10/2002 | Shastri et al. |
| 6,561,143 B2 | 5/2003 | Holtzman |
| 6,569,143 B2 | 5/2003 | Alchas et al. |
| 6,591,124 B2 | 7/2003 | Sherman et al. |
| 6,611,707 B1 | 8/2003 | Prausnitz et al. |
| 6,656,147 B1 | 12/2003 | Gertsek et al. |
| 6,663,820 B2 | 12/2003 | Arias et al. |
| 6,767,341 B2 | 7/2004 | Cho |
| 6,881,203 B2 | 4/2005 | Delmore et al. |
| 6,908,453 B2 | 6/2005 | Fleming et al. |
| 6,923,930 B2 | 8/2005 | Ling et al. |
| 6,926,953 B2 | 8/2005 | Nealey et al. |
| 6,979,347 B1 | 12/2005 | Wu et al. |
| 6,980,855 B2 | 12/2005 | Cho |
| 6,995,336 B2 | 2/2006 | Hunt et al. |
| 7,022,465 B2 | 4/2006 | Heidari |
| 7,041,228 B2 | 5/2006 | Heidari |
| 7,048,723 B1 | 5/2006 | Frazier et al. |
| 7,066,922 B2 | 6/2006 | Angel et al. |
| 7,108,681 B2 | 9/2006 | Gartstein et al. |
| 7,115,108 B2 | 10/2006 | Wilkinson et al. |
| 7,129,554 B2 | 10/2006 | Lieber et al. |
| 7,131,987 B2 | 11/2006 | Sherman et al. |
| 7,137,336 B2 | 11/2006 | Heidari et al. |
| 7,185,663 B2 | 3/2007 | Koch et al. |
| 7,189,435 B2 | 3/2007 | Tuominen et al. |
| 7,195,734 B2 | 3/2007 | Heidari et al. |
| 7,226,439 B2 | 6/2007 | Prausnitz et al. |
| 7,250,037 B2 | 7/2007 | Shermer et al. |
| 7,252,492 B2 | 8/2007 | Olsson et al. |
| 7,285,113 B2 | 10/2007 | Yeshurun |
| 7,315,758 B2 | 1/2008 | Kwiatkowski et al. |
| 7,332,339 B2 | 2/2008 | Canham |
| 7,364,568 B2 | 4/2008 | Angel et al. |
| 7,374,864 B2 * | 5/2008 | Guo ............... B82Y 10/00 264/494 |
| 7,410,476 B2 | 8/2008 | Wilkinson et al. |
| 7,416,541 B2 | 8/2008 | Yuzhakov et al. |
| 7,429,258 B2 | 9/2008 | Angel et al. |
| 7,449,200 B2 | 11/2008 | Sung et al. |
| 7,473,244 B2 | 1/2009 | Frazier et al. |
| 7,531,120 B2 | 5/2009 | Van Rijn et al. |
| 7,537,590 B2 | 5/2009 | Santini, Jr. et al. |
| 7,544,770 B2 | 6/2009 | Haynie |
| 7,556,615 B2 | 7/2009 | Pettis et al. |
| 7,563,451 B2 | 7/2009 | Lin et al. |
| 7,572,405 B2 | 8/2009 | Sherman et al. |
| 7,578,954 B2 | 8/2009 | Gartstein |
| 7,582,069 B2 | 9/2009 | Laurent et al. |
| 7,588,552 B2 | 9/2009 | Yeshurun |
| 7,611,481 B2 | 11/2009 | Cleary et al. |
| 7,627,938 B2 | 12/2009 | Kim et al. |
| 7,651,475 B2 | 1/2010 | Angel et al. |
| 7,658,728 B2 | 2/2010 | Yuzhakov |
| 7,670,127 B2 | 3/2010 | Heidari |
| 7,670,452 B2 | 3/2010 | Heidari et al. |
| 7,687,007 B2 | 3/2010 | Ling et al. |
| 7,704,425 B2 | 4/2010 | Heidari et al. |
| 7,717,693 B2 | 5/2010 | Keil et al. |
| 7,753,888 B2 | 7/2010 | Mukerjee et al. |
| 7,754,131 B2 | 7/2010 | Olsson et al. |
| 7,785,301 B2 | 8/2010 | Yuzhakov |
| 7,803,574 B2 * | 9/2010 | Desai ............... A61L 27/54 424/432 |
| 7,846,488 B2 * | 12/2010 | Johnson ........... A61K 9/0021 324/754.03 |
| 7,855,046 B2 | 12/2010 | Suleski |
| 7,862,849 B2 | 1/2011 | Stellacci et al. |
| 7,901,387 B2 | 3/2011 | Stemme et al. |
| 7,914,480 B2 | 3/2011 | Cleary et al. |
| 7,914,813 B2 | 3/2011 | Adachi et al. |
| 7,918,814 B2 | 4/2011 | Prausnitz et al. |
| 7,972,616 B2 | 7/2011 | Dubrow et al. |
| 7,981,346 B2 | 7/2011 | Griss et al. |
| 7,997,274 B2 | 8/2011 | Baska |
| 8,052,633 B2 | 11/2011 | Kendall |
| 8,057,842 B2 | 11/2011 | Choi et al. |
| 8,088,321 B2 | 1/2012 | Ferguson et al. |
| 8,097,456 B2 | 1/2012 | Borenstein et al. |
| 8,118,753 B2 | 2/2012 | Cho et al. |
| 8,137,697 B1 | 3/2012 | Sung et al. |
| 8,137,736 B2 | 3/2012 | Zhu et al. |
| 8,162,901 B2 | 4/2012 | Gonnelli et al. |
| 8,238,995 B2 | 8/2012 | Chandrasekaran et al. |
| 8,389,205 B2 | 3/2013 | Duerig et al. |
| 8,419,708 B2 | 4/2013 | Tokumoto et al. |
| 8,506,530 B2 | 8/2013 | Laermer et al. |
| 8,574,615 B2 | 11/2013 | Tenney et al. |
| 8,690,838 B2 | 4/2014 | Ozawa et al. |
| 8,915,957 B2 | 12/2014 | Arney et al. |
| 8,944,804 B2 | 2/2015 | Robeson et al. |
| 9,028,409 B2 | 5/2015 | Yodfat et al. |
| 2002/0082543 A1 | 6/2002 | Park et al. |
| 2002/0133129 A1 | 9/2002 | Arias et al. |
| 2002/0183688 A1 | 12/2002 | Lastovich et al. |
| 2003/0045837 A1 * | 3/2003 | Delmore ........... A61B 5/1411 604/173 |
| 2003/0220656 A1 * | 11/2003 | Gartstein ........... A45D 26/0004 606/131 |
| 2004/0028875 A1 | 2/2004 | Van Rijn et al. |

(56) References Cited

U.S. PATENT DOCUMENTS

| | | |
|---|---|---|
| 2004/0063100 A1 | 4/2004 | Wang |
| 2004/0087992 A1 | 5/2004 | Gartstein et al. |
| 2004/0106904 A1 | 6/2004 | Gonnelli et al. |
| 2005/0049625 A1 | 3/2005 | Shaya et al. |
| 2005/0112135 A1 | 5/2005 | Cormier et al. |
| 2005/0118388 A1 | 6/2005 | Kingsford et al. |
| 2005/0119723 A1 | 6/2005 | Peacock |
| 2005/0124967 A1 | 6/2005 | Kaestner et al. |
| 2005/0137531 A1 | 6/2005 | Prausnitz et al. |
| 2005/0143713 A1 | 6/2005 | Delmore et al. |
| 2005/0178760 A1 | 8/2005 | Chang et al. |
| 2005/0187521 A1 | 8/2005 | Fleming et al. |
| 2005/0203613 A1 | 9/2005 | Arney et al. |
| 2006/0024358 A1 | 2/2006 | Santini, Jr. et al. |
| 2006/0025848 A1 | 2/2006 | Weber et al. |
| 2006/0051404 A1 | 3/2006 | Yeshurun et al. |
| 2006/0264893 A1 | 11/2006 | Sage et al. |
| 2007/0066934 A1 | 3/2007 | Etheredge, III et al. |
| 2007/0078376 A1 | 4/2007 | Smith |
| 2007/0081977 A1 | 4/2007 | Horstmann |
| 2007/0088248 A1 | 4/2007 | Glenn et al. |
| 2007/0110810 A1 | 5/2007 | Smith |
| 2007/0112309 A1 | 5/2007 | Zucker |
| 2007/0112548 A1 | 5/2007 | Dickerson et al. |
| 2007/0185432 A1 | 8/2007 | Etheredge, III et al. |
| 2007/0191761 A1 | 8/2007 | Boone et al. |
| 2007/0249552 A1 | 10/2007 | Khalili et al. |
| 2007/0250018 A1 | 10/2007 | Adachi et al. |
| 2007/0260201 A1 | 11/2007 | Prausnitz et al. |
| 2007/0282247 A1 | 12/2007 | Desai et al. |
| 2008/0026464 A1 | 1/2008 | Borenstein et al. |
| 2008/0091226 A1 | 4/2008 | Yeshurun et al. |
| 2008/0097352 A1 | 4/2008 | Beck et al. |
| 2008/0108958 A1 | 5/2008 | Carter et al. |
| 2008/0195035 A1 | 8/2008 | Frederickson et al. |
| 2008/0200883 A1 | 8/2008 | Tomono |
| 2008/0208076 A1 | 8/2008 | Cho et al. |
| 2008/0217180 A1 | 9/2008 | Doye et al. |
| 2008/0221408 A1 | 9/2008 | Hoarau et al. |
| 2008/0262416 A1 | 10/2008 | Duan et al. |
| 2008/0269666 A1 | 10/2008 | Wang et al. |
| 2008/0269685 A1 | 10/2008 | Singh et al. |
| 2008/0305989 A1 | 12/2008 | Wen et al. |
| 2008/0311172 A1 | 12/2008 | Schapira et al. |
| 2008/0312610 A1* | 12/2008 | Binks ............... A61K 9/0021 604/272 |
| 2009/0012494 A1 | 1/2009 | Yeshurun et al. |
| 2009/0043279 A1 | 2/2009 | Kaspar et al. |
| 2009/0069788 A1 | 3/2009 | Yeshurun et al. |
| 2009/0093776 A1 | 4/2009 | Yue et al. |
| 2009/0093871 A1 | 4/2009 | Rea et al. |
| 2009/0093879 A1 | 4/2009 | Wawro et al. |
| 2009/0099427 A1 | 4/2009 | Jina et al. |
| 2009/0099502 A1 | 4/2009 | Tokumoto et al. |
| 2009/0118662 A1 | 5/2009 | Schnall |
| 2009/0137926 A1 | 5/2009 | Srinivasan et al. |
| 2009/0177273 A1 | 7/2009 | Piveteau et al. |
| 2009/0198189 A1 | 8/2009 | Simons et al. |
| 2009/0232870 A1 | 9/2009 | Srivastava et al. |
| 2010/0004733 A1 | 1/2010 | Atansoska et al. |
| 2010/0021464 A1 | 1/2010 | Archambeau et al. |
| 2010/0076035 A1 | 3/2010 | Carter et al. |
| 2010/0121307 A1 | 5/2010 | Lockard et al. |
| 2010/0168506 A1 | 7/2010 | Moon et al. |
| 2010/0215580 A1 | 8/2010 | Hanes et al. |
| 2010/0256568 A1 | 10/2010 | Frederickson et al. |
| 2010/0274203 A1 | 10/2010 | Lee et al. |
| 2010/0316960 A1* | 12/2010 | Duerig ............... B82Y 10/00 430/322 |
| 2011/0021996 A1 | 1/2011 | Lee et al. |
| 2011/0046557 A1 | 2/2011 | Lee et al. |
| 2011/0059150 A1 | 3/2011 | Kendall et al. |
| 2011/0144591 A1 | 6/2011 | Ross et al. |
| 2011/0160069 A1 | 6/2011 | Corrie et al. |
| 2011/0270221 A1 | 11/2011 | Ross |
| 2012/0089117 A1 | 4/2012 | Junginger et al. |
| 2012/0109065 A1 | 5/2012 | Backes |
| 2012/0114734 A1 | 5/2012 | Desai et al. |
| 2012/0128932 A1 | 5/2012 | Veith et al. |
| 2013/0144257 A1 | 6/2013 | Ross |
| 2013/0150822 A1 | 6/2013 | Ross |
| 2013/0158505 A1 | 6/2013 | Ross |
| 2013/0165861 A1 | 6/2013 | Ross |
| 2013/0211310 A1* | 8/2013 | Bommarito ............ B08B 17/06 602/48 |
| 2013/0331792 A1 | 12/2013 | Karp et al. |
| 2014/0112921 A1 | 4/2014 | Ross |
| 2014/0287019 A1 | 9/2014 | Ollerenshaw et al. |
| 2014/0343532 A1 | 11/2014 | Ross |

FOREIGN PATENT DOCUMENTS

| | | |
|---|---|---|
| JP | H08-337521 | 12/1996 |
| JP | 2008511382 | 4/2008 |
| JP | 2009-207733 | 9/2009 |
| JP | 2010-505518 | 2/2010 |
| WO | WO 99/45860 | 9/1999 |
| WO | WO 00/74764 | 12/2000 |
| WO | WO 01/75164 A2 | 10/2001 |
| WO | WO 02/30506 A2 | 4/2002 |
| WO | WO 02/32480 A2 | 4/2002 |
| WO | WO 03/020359 A2 | 3/2003 |
| WO | WO 03/024508 A2 | 3/2003 |
| WO | WO 2005/049128 A1 | 6/2005 |
| WO | WO 2006/062974 | 6/2006 |
| WO | WO 2006/062974 A2 | 6/2006 |
| WO | WO 2006/075689 A1 | 7/2006 |
| WO | WO 2007/012114 A1 | 2/2007 |
| WO | WO 2007/081876 | 7/2007 |
| WO | WO 2007/112309 A2 | 10/2007 |
| WO | WO 2008/003564 | 1/2008 |
| WO | WO 2008/003564 A1 | 1/2008 |
| WO | WO 2008/024141 | 2/2008 |
| WO | WO 2008/024141 A2 | 2/2008 |
| WO | WO 2009/079589 | 6/2009 |
| WO | WO 2009/079589 A2 | 6/2009 |
| WO | WO 2009/113856 | 9/2009 |
| WO | WO 2010/070628 A1 | 6/2010 |
| WO | WO 2010/087971 | 8/2010 |
| WO | WO 2010/126640 | 11/2010 |
| WO | WO 2011/116388 A1 | 9/2011 |
| WO | WO 2011/135531 | 11/2011 |
| WO | WO 2011/135531 A | 11/2011 |
| WO | WO 2012/006677 | 1/2012 |
| WO | WO 2012/046149 A1 | 4/2012 |
| WO | WO 03/092785 | 7/2016 |

OTHER PUBLICATIONS

Ainslie et al., "Microfabricated implants for applications in therapeutic delivery, tissue engineering, biosensing." *Royal Society of Chemistry.* 8. (2008): 1864-1878.

Ainslie et al., "Microfabricated Devices for Enhanced Bioadhesive Drug Delivery: Attachment to and Small-Molecule Release Through a Cell Monolayer Under Flow." *Small.* (2009).

Bekarde, Lil Gercek. "Biomimetic Apatite-coated PCL Scaffolds: Effect of Surface Nanotopography on Cellular Functions." *Journal of Bioactivve and Compatible Polymers.* 24.6 (2009): 507-524.

Berry et al., "The interaction of human bone marrow cells in nanotopographical features in three dimensional constructs." *Journal of Biomedical Materials Research Part A.* 79A.2 (2006): 431-439.

Biehl et al., "Proliferation of Mouse Embryonic Stem Cell Progeny and the Spontaneous Contractile Activity of Cardiomyocytes Are Affect by Microtopography." *Developmental Dynamics* . 238. (2009): 1964-1973.

Brunauer et al., "Adsorption of Gases in Multimolecular Layers." *Journal of the American Chemical Society.* 60. (1938): 309-319.

Chandler, David L., "PhysOrg.com." *Harnessing nanopatterns: Tiny textures can produce big differences.* N.p., Sep. 24, 2009. Web. Dec. 1, 2009. <http://www.physorg.com/news173004362.html>.

(56) References Cited

OTHER PUBLICATIONS

Choi et al. "Cell interaction with three-dimensional sharp-tip nanotopography." *Biomaterials.* 28.9 (2007): 1672-1679.
Chun et al., "The role of polymer nanosurcace roughness and the submicron pores in improving blatter urothelial cell density and inhibiting calcium ocalate stone formation." *Nanotechnology.* 20.8 (2009): 85104.
Citi, Si., "Protein Kinase Inhibitors Prevent Junction Dissociation Induced by Low Extracellular Calcium in MDCK Epithelial Cells", J Cell Biology, 1992, 117(1) 169-178.
Cohn, Abby. "Drug Delivery, Nanoscale." *Innovations.* 3.4 (2009).
Curtis et al., "Cell signaling arising from nanotopography: implications for nanomedicaldevices." *Nanomedicine.* 1.1 (2006): 67-72.
Dalby, Matthew J. "Nanostructured surfaces: cell engineering and cell biology." *Nanomedicine.* 4.3 (2009): 247-248.
Dalby et al., "Attempted endocytosis colloidal lithography by human fibroblasts," *Experimental Cell Research.* 295. (2004): 387-394.
Dalby et al., "Nano-Topography Induces Mechanotransductino in Human Fibroblasts." *European Cells and Materials* . 6.2 (2003): 31.
Dalby et al., "Increasing Fibroblast Response to Materials Using Nanotopography: Morphological and Genetic measurements of Cell Response to 13-nm-High Polymer Demixed Islands." *Experimental Cell Research.* 276.1 (2002): 1-9.
Fischer et al., "Biometric Nanowire Coatings for Next Generation Adhesive Drug Delivery Systems." *Nano Letters.* 9.2 (2009): 716-720.
Geiger & Ayalon, "Cadherins", Annu Rev Cell Biol. 1992, 8:307-32.
Gumbiner & Simons, "A Functional Assay for Proteins Involved in Establishing and Epithelial Occluding Barrier: Identification of an Uvomorulin-like Polypetide", J. Cell Biology, 1986, 102: 457-468.
Hart et al., "Filapodial Sensing of Nanotopography in Osteoprogenitor Cells." *European Cells and Materials* . 10.2 (2005): 65.
He, et al., "The anatase phase of nanotopography titania plays an important role on osteoblast cell morphology and proliferation", *Journal of Mater. Sci: Mater Med* (2008). 19:3465-3472.
Hirano et al., "Calcium-dependent Cell-Cell Adhesion Molecules (Cadherins): Subclass Specificities and Possible Involvement of Actin Bundles", J. Cell Biology, 1987, 105(6): 2501-2510.
Hu et al., "Surface Energy Induced Patterning of Polymer Nanostructures for Cancer Diagnosis and Therapy." *IEEE Nano 2007 Conference Paper.* (2007).
Kaushal et al, Influence of Piperline on Transcutaneous Permeation of Repaglinide in Rats and on Tight Junction Proteins in HaCaT Cells: Unveiling the Mechanisms for Enhanced Permeation; Sci. Pharm. 2009; 77; 877-897.
Kitner, C., "Regulation of embryonic cell adhesion by the cadherin cytoplasmic domain", Cell, 1992, 69(2):225-36.
Korhonen et al., "Nitric oxide production and signalling in inflammation", Curr Drug Targets Inflamm Allergy 4(4): 471-9, 2005.
Langeler et al., "Norepinephrine and iloprost improve barrer function of human endothelial cellmonolayers: role of cAMP", Am J Physio Cell Physiol, 1991, vol. 260(5). C1052-C1059.
Lim et al., "Human foetal osteoblastic cell response to polymer-demixed nanotopographic interfaces." *Journal of Royal Society Interface.* 2.2 (2005): 97-108.
Madara, JL, "Regulation of the movement of solutes across tight junctions", Annu Rev Physiol, 1998. 60:143-59.
Mahdavi et al., "A biodegradable and biocompatible gecko-inspired tissue adhesive." *PNAS.* 105.7 (2008): 2307-2312.
Martinez-Palomo et al., "Experimental Modulation of Occluding Junctions in a Cultured Transporting Epithelium", J. Cell Biology, 1980, 87: 736-745.
Meirelles et al., "The effect of chemical and nanotopographical modifications on the early stages of osseointegration." *International Journal of Oral and Maxillofacial Implants.* 23.4 (2008): 641-647.

Mendelsohn et al., "Inorganic Nanoporous Membranes for Immunoisolated Cell-Based Drug Delivery." *Therapeutic Applications of Cell Microencapsulation.*
Nagafuchi & Takechi, "Cell binding function of E-cadherin is regulated by the cytoplasmic domain", EMBO Journal, 1988, 7(12): 3679-3684.
Ng et al., "Study of substrate topographical effects on epithelial cell behavior using etched alpha—particle tracks on PADC films." *Nuclear instruments and Methods in Physics Research Section B: Beam Interactions with Materials and Atoms.* 266.14 (2008): 3247-3256.
Ojakian, GK, "Tumor promotor-induced changes in the permeability of cell tight junctions", Cell. 1981, 23(1): 95-103.
Orr et al., "Submicrometer and Nanoscale Inorganic Particles Exploit the Actin Machinery to Be Propelled along Microvilli-likestructures into Alveolar Cells." *American Chemical Society NANO.* 1.5 (2007): 463-475.
Ozawa et al., "The cytoplasmic domain of the cell adhesion molecule uvomorulin associations with three independnet proteins structurally related in different species". EMBO Journal. 1989, 8(6): 1711-1717.
Ozawa et al., "Uvomorulin-catenin complex formation is regulated by a specific domain in the cytoplasmic region of the cell adhesion molecule", Dev Biology, 1990, 87: 4246-4250.
Peng et al., "Long-Term Small Molecule and Protein Elution from $TiO_2$ Nanotubes." *Nano Letters.* 9.5 (2009): 1932-1936.
Peng et al., "The effect of $TiO_2$ nanotubes on endothelial function and smooth muscle proliferation." *Journal of Biomaterials.* 30. (2009): 1268-1272.
Rubin et al., "A Cell Culture Model of the Blood-Brain Barrier", J. Cell Biology, 1991, 115:1725-1735.
Rubin, LL, "Endothelial cells: adhesion and tight junctions", Curr Opin Cell Biol, 1992, 4(5):830-3.
Rutten et al., "Electrical resistance and macromolecular permeability of brain endothelial monolayer cultures", Brain Res, 1987, 425(2):301-10.
Sapra et al., "Transdermal Delivery of Carvedilol Containing Glycyrrhizin and Chitosan as Permeation Enhancers:Biochemical, Biophysical, Microscopic and Pharmacodynamic Evaluation." *Drug Delivery* . 15.7 (2008): 443-454.
Sapra et al., "Transdermal delivery of carvedilol in rats: probing the percutaneous permeation enhancement mechanism of soybean extract-chitosan mixture." *Drug Delivery* . 35.10 (2009): 1230-1241.
Sapra et al., "Effect of Asparagus racemous Extract on Transdermal Delivery of Carvedilol: A Mechanistic Study." *American Association of Pharmaceutical Scientists PharmSciTech.* 10.1 (2009): 199.
Schubert et al., "Sliding-Induced adhesion of stiff polymer microfibre arrays. II. Microscale behavior", J Royal Society; Jan. 2008, 5, 845-853.
Stappert et al, "A short core region of E-cadherin is essential for certain binding and is highly phosphorylated", 1993, Cell Adhes Commun, 2(4): 319-27.
Stelzner et al., "Role of cyclic adenosine monophosphate in the induction of endothelial barrier properties", J. Cell Physiol, 1989, 139(1):157-66.
Teo et al., "The effect of micro and nanotopography on endocytosis in drug and gene delivery systems", *Biomaterials*, 32 (2011). 9866-9875.
Thakar et al., "Contractility-Dependent Modulation of Cell Proliferation and Adhesion by Microscale Topographical Cues." *Small.* 4.9 (2008): 1416-1224.
Valenta et al., "The use of polymers for dermal and transdermal delivery." *European Journal of Pharmaceutics and Biopharmaceutics.* 58.2 (2004): 279-289.
Wang et al., "Nano patterned PDMS for periodontal ligament fibroblast culture." *Surface and Coatings Technology.* 204.4 (2009): 525-530.
Wei et al., "Protein adsorption on materials surfaces with nanotopography." *Chinese Science Bulletin.* 52.23 (2007): 3169-3173.
Wood, M.A. "Colloidal lithography and current fabrication techniques producing in-plane nanotopography for biological applications." *Journal of the Royal Society Interface.* 4.12 (2007): 1-17.

(56) References Cited

OTHER PUBLICATIONS

Yao et al., "Nano-Surface Modification on Titanium Implants for Drug Delivery." *Materials Research Society* . (2007).
Yim et al., "Nanopattern-induced changes in morphology and motility of smooth muscle cells." *Journal of Biomaterials.* 58.1 (2005).
Abstract of Japanese Patent—JP2008237673, Oct. 9, 2008, 1 page.
Abstract of Japanese Patent—JP2009207733, Sep. 17, 2009, 1 page.
Abstract of Japanese Patent—JPH08337521, Dec. 24, 1996, 2 pages.
Inkyu Park et al., Towards the silicon nanwire-based sensor for intracellular biochemical detection, 6 pages, Apr. 1, 2007, Biosensors and Bioelectronics, vol. 22, No. 9-10.
Supplementary European Search Report dated Jan. 2, 2014, 5 pages.
Al-Qallaf et al., "Optimizing Microneedle Arrays to Increase Skin Permeability for Transdermal Drug Delivery," Interdisciplinary Transport Phenomena V: Ann. N.Y. Acad. Sci., 2009, pp. 1-12.
Berliner et al., "Impact of Transdermal Fentanyl on Quality of Life in Rheumatoid Arthritis", Clinical Journal of Pain, 2007, 23(6): 530-534.
Abstract of Japanese Patent—JP2008511382, Apr. 17, 2008, 2 pages.
Abstract of Japanese Patent—JP2001238964, Sep. 4, 2001, 1 page.
Biggs et al., "Interactions with Nanoscale Topography: Adhesion quantification and signal transduction in cells of osteogenic and multipotent lineage," Journal of Biomedical Materials Research Part A, 2008, pp. 195-208.
Kumar et al. "Transdermal Drug Delivery System: An Overview," International Journal of Pharmaceutical Sciences Review and Research. 3.2 (2010): 49-54.
Verma et al., "Development of Transdermal Drug Dosage Formulation for the Anti-Rheumatic Ayurvedic Medicianal Plants", Ancient Sci. Life, 2007; 11:66-9.

\* cited by examiner square packing hexagonal packing

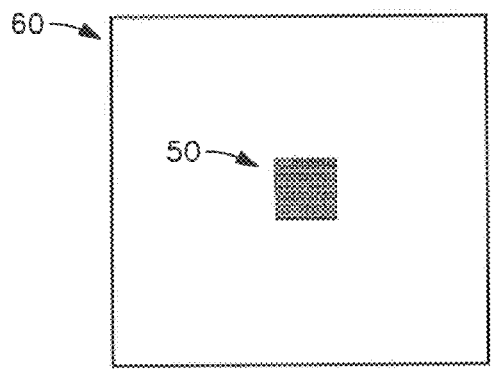
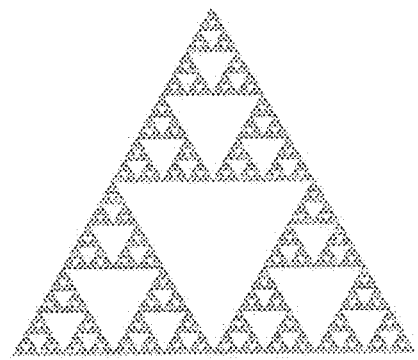
FIG. 13    FIG. 16
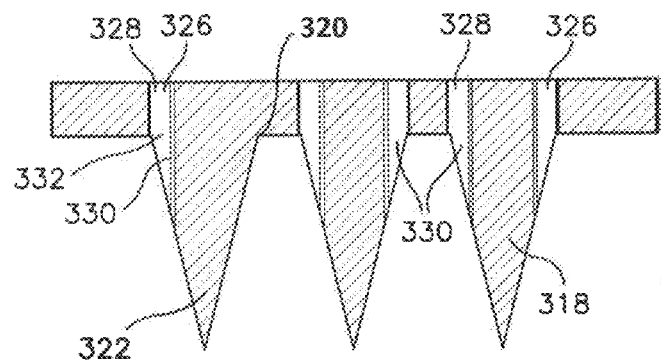
FIG. 14
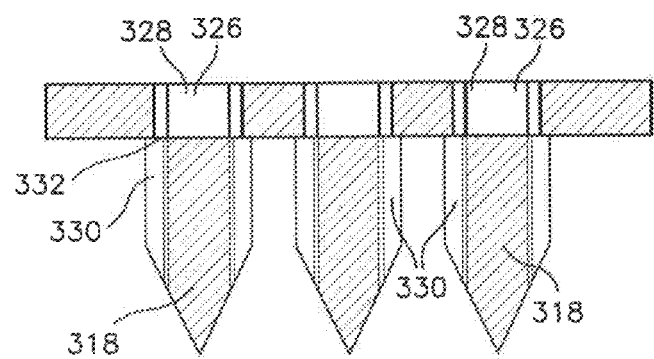
FIG. 15

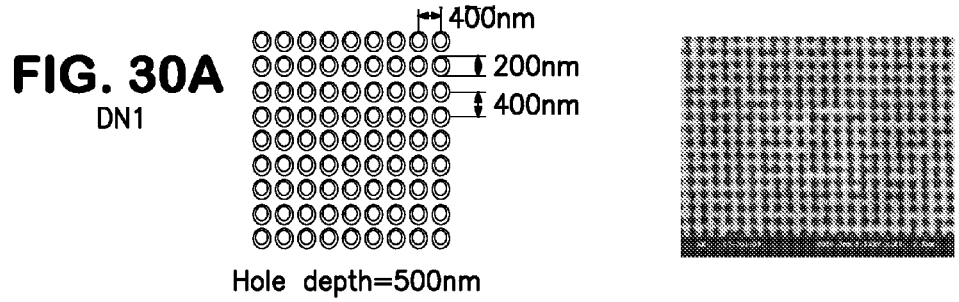
FIG. 30A DN1 Hole depth=500nm
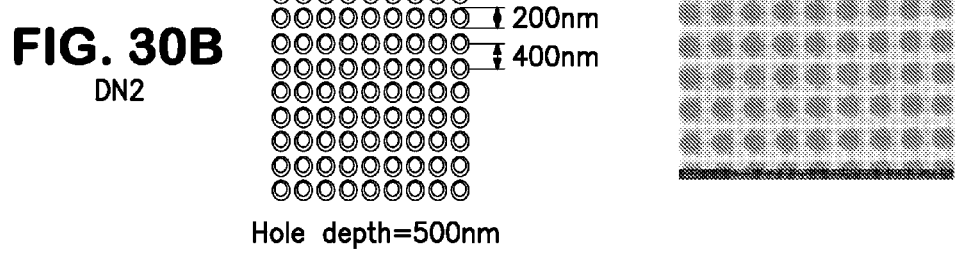
FIG. 30B DN2 Hole depth=500nm
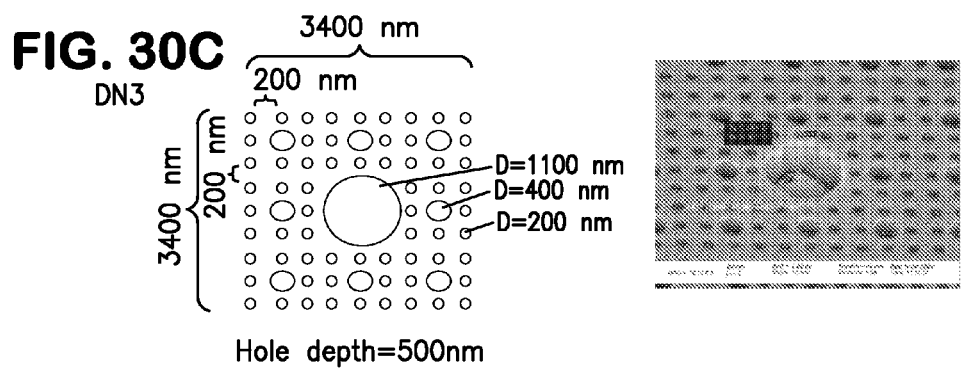
FIG. 30C DN3 Hole depth=500nm
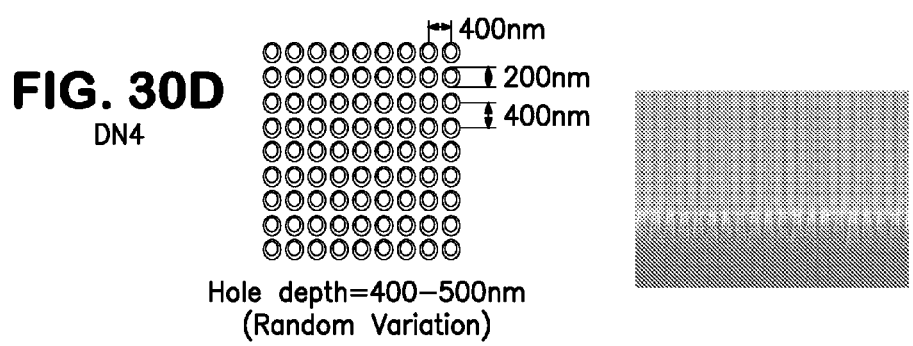
FIG. 30D DN4 Hole depth=400-500nm (Random Variation)

FIG. 30E
NTTAT2
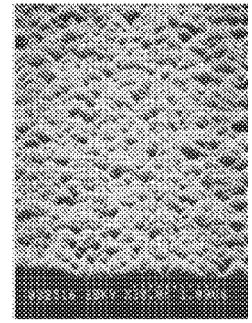
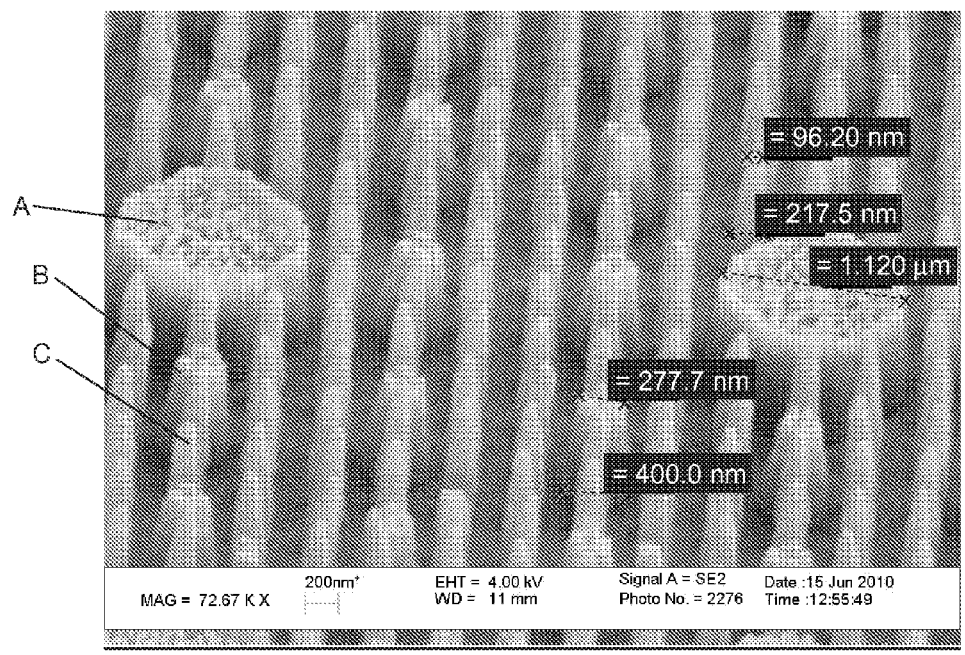
FIG. 31

INJECTION MOLDED MICRONEEDLE ARRAY AND METHOD FOR FORMING THE MICRONEEDLE ARRAY

CROSS REFERENCE TO RELATED APPLICATIONS

This application claims priority to U.S. Provisional Patent Application Ser. No. 61/328,723 having a filing date of Apr. 28, 2010, U.S. Provisional Patent Application Ser. No. 61/411,071 having a filing date of Nov. 8, 2010, and U.S. Provisional Patent Application Ser. No. 61/435,939 having a filing date of Jan. 25, 2011, all of which are incorporated herein in their entirety by reference.

BACKGROUND

Primary drug delivery methods include oral delivery and injections, but both methods present difficulties. For instance, injections are painful and both methods tend to provide bursts of agents rather than a preferred steady-state delivery. Additionally, the successful long term use of both oral delivery and injected delivery requires the patient to consistently meet the time requirements for the delivery method.

Transdermal delivery materials have been developed in an attempt to provide a painless route for delivery of active agents over a sustained period with little or no interruption of the patient's daily routine. Unfortunately, natural dermal characteristics such as the overlapping corneocytes of the stratum corneum, the tight junction of the stratum granulosum, and Langerhans cells of the stratum spinosum that institute an immune response and/or a foreign body response all present barriers to successful transdermal delivery of an active agent.

The utilization of microneedles to facilitate transdermal delivery of active agents has improved this delivery route. A microneedle transdermal device includes an array of needles that may penetrate at least the stratum corneum and reach an underlying layer of the skin. In some devices, the microneedles are designed so as to penetrate to a depth that does not stimulate the nerve endings and institute a pain response. Examples of microneedle devices have been described in U.S. Pat. No. 6,334,856 to Allen, et al. and U.S. Pat. No. 7,226,439 to Prausnitz, et al., both of which are incorporated herein by reference.

In order to take full advantage of microneedle devices, efficient methods for mass production of devices that may deliver a wide array of agents need to be developed. Attempts have been made to form microneedle arrays by injection molding processes. For instance, U.S. Patent Application Publication No. 2007/0191761 to Boone, et al. describes a method including injecting a moldable material into a negative mold insert that is characterized by a negative image of a microneedle. U.S. patent Application Publication No. 2008/0088066 to Ferguson, et al. describes a method that utilizes a mold apparatus including a mold insert that has a negative image of a microneedle and a compression core. The mold housing allows reciprocal motion between the mold insert and the compression core and when the housing is in a closed position, a polymeric material is injected into the closed apparatus.

Unfortunately, even with the inclusion of injection molded microneedles, transdermal devices are presently limited to delivery of low molecular weight agents that have a moderate lipophilicity and no charge. Even upon successful crossing of the natural dermal boundary, problems still exist with regard to maintaining the activity level of delivered agents and avoidance of foreign body and immune response.

What are needed in the art are microneedle devices that may be utilized for delivery of a wide variety of agents, including high molecular weight agents. What is also needed in the art is an efficient method for forming the devices that may be translated to a mass production facility, such as an injection molding method.

Summary

Disclosed in one embodiment is a method of forming a microneedle array. A method may include injecting a moldable material into a microneedle negative cavity, wherein the microneedle negative cavity defines a plurality of fabricated nanostructures on a surface, the nanostructures being arranged in a pattern.

Also disclosed is an injection molded microneedle array. The microneedle array may include a substrate, a plurality of microneedles extending from a surface of the substrate, and a plurality of nanostructures on a surface of at least one of the microneedles. The plurality of nanostructures may be arranged in a predetermined pattern. A transdermal patch including the injection molded microneedle array is also disclosed.

BRIEF DESCRIPTION OF THE DRAWINGS

A full and enabling disclosure of the subject matter, including the best mode thereof, directed to one of ordinary skill in the art, is set forth more particularly in the remainder of the specification, which makes reference to the appended figures in which:

FIG. 13 schematically illustrates a mold including a single microneedle array.

FIGS. 14 and 15 are partial cross-sectional views of microneedle arrays that may be formed in accordance with an embodiment of the present disclosure.

FIG. 16 illustrates a Sierpinski triangle fractal.

FIGS. 30A-30E illustrate several nanotopography patterns as described herein.

FIG. 31 is an SEM of a film including a nanopatterned surface.

DETAILED DESCRIPTION OF REPRESENTATIVE EMBODIMENTS

Reference now will be made in detail to various embodiments of the disclosed subject matter, one or more examples of which are set forth below. Each example is provided by way of explanation, not limitation. In fact, it will be apparent to those skilled in the art that various modifications and variations may be made in the present disclosure without departing from the scope or spirit of the subject matter. For instance, features illustrated or described as part of one embodiment may be used on another embodiment to yield a still further embodiment. Thus, it is intended that the present disclosure covers such modifications and variations as come within the scope of the appended claims and their equivalents.

In general, disclosed herein is an injection molding process for forming a microneedle array and the injection molded arrays formed according to the process. More specifically, the injection molded microneedle array may include a pattern of structures fabricated on a surface of the needles, at least a portion of which are nanostructures fabricated on a nano-sized scale. As utilized herein, the term 'fabricated' generally refers to a structure that has been specifically designed, engineered, and/or constructed so as to exist at a surface of the microneedle and is not to be equated with a surface feature that is merely an incidental product of the injection molding formation process. Thus, there will be a predetermined pattern of nanostructures on the surface of the microneedles.

The injection molded microneedle array may be formed according to a process that utilizes multiple mold segments to form each microneedle. More specifically, each mold segment defines at least one microneedle segment. Mold segments may be aligned with one another to form a complete mold. Mold segments are aligned such that the microneedle segments on the adjacent mold segments are also aligned with one another. Upon alignment of two or more microneedle segments, a complete microneedle cavity may be defined, with each microneedle segment defining a portion of the complete microneedle cavity. In addition, the microneedle segments may define upon a surface the predetermined pattern of nanostructures.

Figure 1:
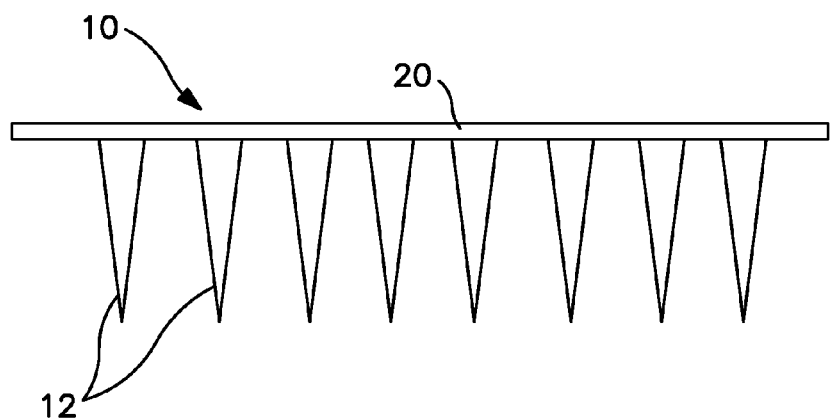
FIG. 1 schematically illustrates one embodiment of a microneedle device.
Figure 2:
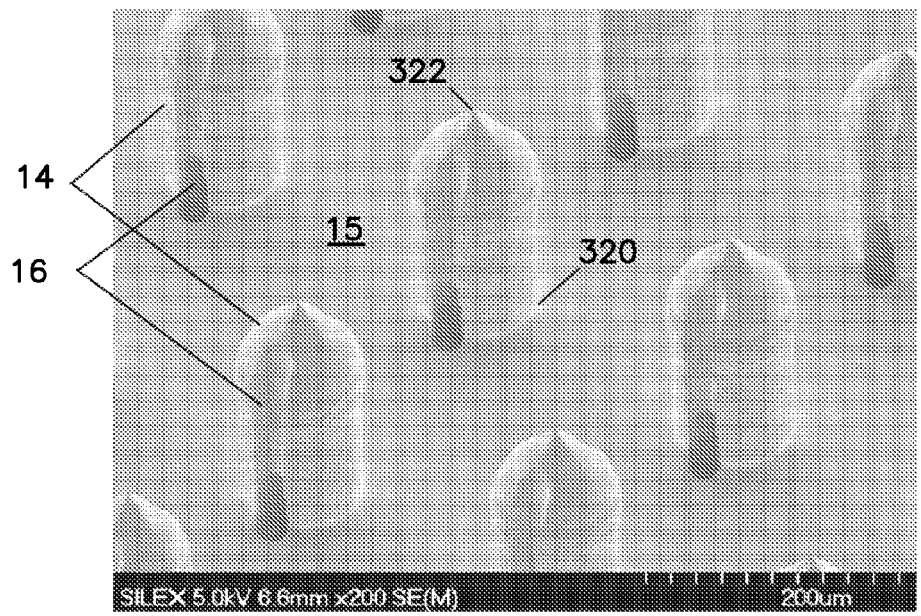
FIG. 2 is a scanning electron micrograph (SEM) image of another embodiment of a microneedle device.

FIG. 1 illustrates a typical microneedle array 10. As may be seen, the array includes multiple individual needles 12; each formed to a size and shape so as to penetrate a biological barrier without breakage of the individual microneedles. Microneedles may be solid, porous, or may include a hollow portion. A microneedle may include a hollow portion, e.g., an annular bore that may extend throughout all or a portion of the needle, extending parallel to the direction of the needle axis or branching or exiting at a side of the needle, as appropriate. For example, FIG. 2 illustrates an array of microneedles 14 each including a channel 16 along a length of the needles as may be utilized for, e.g., delivery of an agent to a subdermal location. For instance, a channel 16 may be in at least partial alignment with an aperture in base 15 so as to form a junction between the aperture and channel 16 allowing the passage of a substance through the channel 16.

Figure 3:
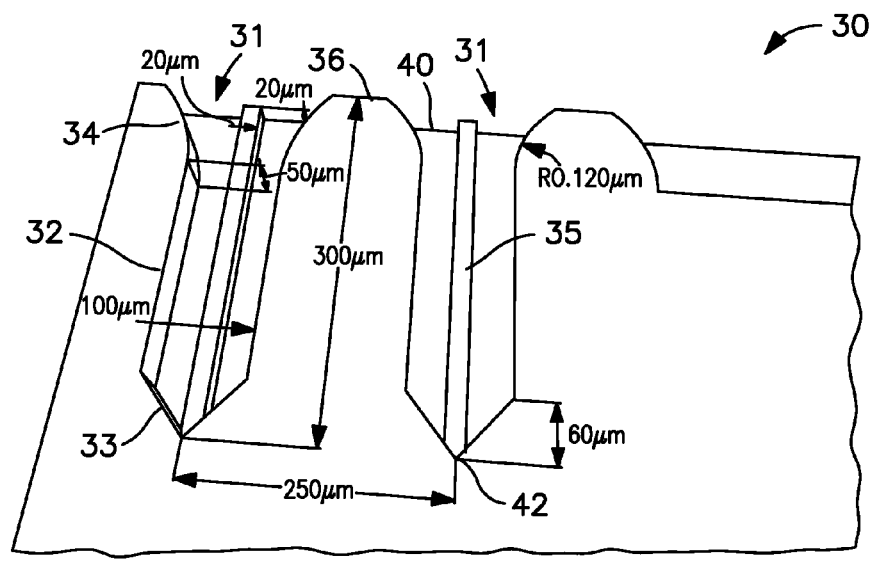
FIG. 3 schematically illustrates one mold segment, the mold segment including two microneedle segments.

An injection molded microneedle array may be formed by use of a mold that defines on a surface of a microneedle a predetermined pattern including nanostructures. In one embodiment, the mold may be formed from a plurality of aligned mold segments. FIG. 3 schematically illustrates one embodiment of a single mold segment 30 including two adjacent microneedle segments 31. Each microneedle segment 31 defines only a portion of a single microneedle. A complete negative cavity for a microneedle will be formed by alignment of microneedle segments that are on adjacent mold segments.

The microneedle negative mold cavity may provide a microneedle of any desired geometry. For instance, the microneedle formed from a microneedle segment 31 may generally conform to the shape of the microneedle segment 31 that includes a straight (untapered) portion 32, a tapered tip portion 33, and a tapered base portion 34. A microneedle segment may alternatively have a shaft that is straight along the entire length or a tapered shaft. In one embodiment, the cross section of a microneedle segment may be greatest at the base end of the microneedle segment and taper to a point at the end distal the base.

A microneedle segment may define a portion of a microneedle shaft that is circular or non-circular in cross-section. For example, the cross-section of a molded microneedle may be polygonal (e.g. star-shaped, square, triangular), oblong, or any other shape.

The size of individual microneedle mold segments 31 may be optimized depending upon the desired size of the microneedle, for instance depending upon the targeting depth of the microneedle, the strength requirements of the needle to avoid breakage in a particular tissue type, etc. For instance, the cross-sectional dimension of mold segments 31 are 100 micrometers, but an injection molded transdermal microneedle may have a cross sectional dimension between about 10 nm and 1 millimeter, or between about 1 micrometer and about 200 micrometers, or between about 10 micrometers and about 100 micrometers.

An array of microneedles need not include microneedles that are all identical to one another. An array may include a mixture of microneedles having various lengths, outer diameters, inner diameters, cross-sectional shapes, nanostructured surfaces, and/or spacings between the microneedles. For example, the microneedles may be spaced apart in a uniform manner, such as in a rectangular or square grid or in concentric circles. The spacing may depend on numerous factors, including height and width of the microneedles, as well as the amount and type of any substance that is intended to be moved through the microneedles. While a variety of arrangements of microneedles is useful, a particularly useful arrangement of microneedles is a "tip-to-tip" spacing between microneedles of about 50 micrometers or more, in some embodiments about 100 to about 800 micrometers, and in some embodiments, from about 200 to about 600 micrometers.

The size and shape of the microneedles may also vary as desired. For example, the microneedle segments 31 of FIG. 3 include a rectangular portion 32 upon which is positioned a tip portion 33 having a tapering edge. In alternative embodiments, however, the microneedles formed by use of a microneedle segment may have a cylindrical shaft and a conical tip portion, or may have an overall pyramidal shape or an overall conical shape. Regardless, the microneedle mold segment 31 typically includes a base 40 and a tip 42. As shown in FIG. 2 for a formed microneedle, the base 320 is the portion of the microneedle 14 that is proximate to the surface of the support 15. The tip 322 of the microneedle 14 is the point of the microneedle that is furthest from the base 320. Although the tip 322 may be variously formed, it typically has a radius that is less than or equal to about 1 micrometer.

The microneedles formed by a microneedle segment 31 are typically of a length sufficient to penetrate the stratum corneum and pass into the epidermis, but not penetrate through the epidermis and into the dermis in applications where it is desirable to minimize pain. In certain embodiments, the microneedle segments 31 have a length (from their tip 42 to their base 36) between about 1 micrometer and about 1 millimeter in length, for instance about 500 micrometers or less, in some embodiments from 10 to about 500 micrometers, and in some embodiments, from about 30 to about 200 micrometers.

A microneedle segment 31 of a negative mold cavity may define features of a microneedle. For instance, in an embodiment in which a microneedle is formed that defines a bore or a channel for passage of an agent therethrough during use, a microneedle segment 31 may include a microneedle channel mold 35 so as to form a channel along a length of a microneedle, for instance as is illustrated in FIG. 2 at 16.

Upon injection of the formable material to the cavity, the channel mold may form a channel along a length of the nascent microneedle.

The dimensions of the channel 16, when present, may be specifically selected to induce capillary flow of a drug compound. Capillary flow generally occurs when the adhesive forces of a fluid to the walls of a channel are greater than the cohesive forces between the liquid molecules. Specifically, capillary pressure is inversely proportional to the cross-sectional dimension of the channel 16 and directly proportional to the surface tension of the liquid, multiplied by the cosine of the contact angle of the fluid in contact with the material forming the channel. Thus, to facilitate capillary flow in the patch, the cross-sectional dimension (e.g., width, diameter, etc.) of the channel 16 may be selectively controlled, with smaller dimensions generally resulting in higher capillary pressure. For example, in some embodiments, the cross-sectional dimension of the channel typically ranges from about 1 micrometer to about 100 micrometers, in some embodiments from about 5 micrometers to about 50 micrometers, and in some embodiments, from about 10 micrometers to about 30 micrometers. The dimension may be constant or it may vary as a function of the length of the channel 16. The length of the channel may also vary to accommodate different volumes, flow rates, and dwell times for the drug compound. For example, the length of the channel may be from about 10 micrometers to about 800 micrometers, in some embodiments from about 50 micrometers to about 500 micrometers, and in some embodiments, from about 100 micrometers to about 300 micrometers. The cross-sectional area of the channel may also vary. For example, the cross-sectional area may be from about 50 square micrometers to about 1,000 square micrometers, in some embodiments from about 100 square micrometers to about 500 square micrometers, and in some embodiments, from about 150 square micrometers to about 350 square micrometers. Further, the aspect ratio (length/cross-sectional dimension) of the channel may range from about 1 to about 50, in some embodiments from 5 to about 40, and in some embodiments from about 10 to about 20. In cases where the cross-sectional dimension (e.g., width, diameter, etc.) and/or length vary as a function of length, the aspect ratio can be determined from the average dimensions.

Microneedle segments 31 may be formed such that they are oriented at any suitable angle to the base 36 of the mold segment, the base 36 forming a surface of a supporting substrate. In one embodiment, the microneedle segments 31 may be oriented perpendicular to the base 36 and a larger density of microneedles per unit area of substrate may be formed. However, this is not a requirement, and the angle of the microneedle segments 31 with respect to the base 36, where the formed microneedles will join a substrate, may be varied to orient the injection molded microneedles on the supporting substrate as desired.

Figure 4:
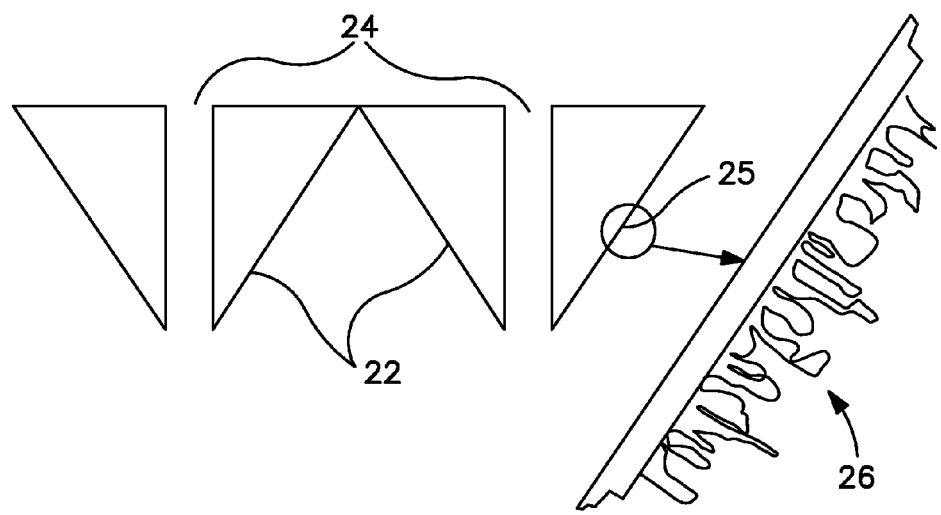
FIG. 4 schematically illustrates one embodiment of a microneedle including a surface that defines a nanotopography that may interact with an extracellular matrix (ECM).

In addition to a channel mold 36, a microneedle segment 31 may define on a surface a plurality of fabricated nano-sized structures or negative nano-sized structures that may form a predetermined pattern including nanostructures (a nanotopography) on a surface of an injection molded microneedle. FIG. 4 schematically illustrates the ends of two representative microneedles 22 that include fabricated nanostructures on a surface. In this particular embodiment, microneedles 22 define a central bore 24 as may be used for delivery of an agent via the microneedles 22. The surface 25 of microneedle 22 defines nanotopography 26 thereon. In this particular embodiment, the nanotopography 26 defines a random pattern on the surface 25 of the microneedle 22.

When forming microneedles that include fabricated nanotopography thereon, a microneedle segment 31 may include a pattern of a plurality of identical structures formed on the surface or may include a pattern of multiple different structures formed of various sizes, shapes and combinations thereof. A predetermined pattern of structures may include a mixture of structures having various lengths, diameters, cross-sectional shapes, and/or spacings between the structures. For example, the structures may be spaced apart in a uniform manner, such as in a rectangular or square grid or in concentric circles. In one embodiment, the pattern components may vary with regard to size and/or shape and may form a complex nanotopography. In one embodiment a complex nanotopography may define a fractal or fractal-like geometry.

As utilized herein, the term "fractal" generally refers to a geometric or physical structure having a fragmented shape at all scales of measurement between a greatest and a smallest scale such that certain mathematical or physical properties of the structure behave as if the dimensions of the structure are greater than the spatial dimensions. Mathematical or physical properties of interest may include, for example, the perimeter of a curve or the flow rate in a porous medium. The geometric shape of a fractal may be split into parts, each of which defines self-similarity. Additionally, a fractal has a recursive definition and has a fine structure at arbitrarily small scales.

As utilized herein, the term "fractal-like" generally refers to a geometric or physical structure having one or more, but not all, of the characteristics of a fractal. For instance, a fractal-like structure may include a geometric shape that includes self-similar parts, but may not include a fine structure at an arbitrarily small scale. In another example, a fractal-like geometric shape or physical structure may not decrease (or increase) in scale equally between iterations of scale, as may a fractal, though it will increase or decrease between recursive iterations of a geometric shape of the pattern. A fractal-like pattern may be simpler than a fractal. For instance, it may be regular and relatively easily described in traditional Euclidean geometric language, whereas a fractal may not.

The structures on a molded microneedle may all be formed with the same general shape (e.g., pillars) and to the same or different scales of measurement (e.g., nano-scale pillars as well as micro-scale pillars). Alternatively, the structures may vary in both size and shape or may vary only in shape while formed to the same nano-sized scale. Additionally, structures may be formed in an organized array or in a random distribution. At least a portion of the structures may be nanostructures formed on a nano-sized scale, e.g., defining a cross-sectional dimension of less than about 500 nm, for instance less than about 400 nm, less than about 250 nm, or less than about 100 nm. The cross sectional dimension of the nanostructures may generally be greater than about 5 nanometers, for instance greater than about 10 nanometers, or greater than about 20 nanometers. For example, the nanostructures may define a cross sectional dimension between about 5 nanometers and about 500 nanometers, between about 20 nanometers and about 400 nanometers, or between about 100 nanometers and about 300 nanometers. In cases where the cross sectional dimension of a nanostructure varies as a function of height of the nanostructure, the cross sectional dimension can be determined as an average from the base to the tip of the nanostructures, or as the maximum cross sectional dimension of the structure, for example the cross sectional dimension at the base of a cone-shaped nanostructure.

FIG. 4 illustrates one embodiment of a complex nanotopography as may be formed on a surface. This particular pattern includes a central large pillar 100 and surrounding pillars 102, 104, of smaller dimensions provided in a regular pattern. As may be seen, this pattern includes an iteration of pillars, each of which is formed with the same general shape, but vary with regard to horizontal dimension. This particular complex pattern is an example of a fractal-like pattern that does not include identical alteration in scale between successive recursive iterations. For example, while the pillars 102 are first nanostructures that define a horizontal dimension that is about one third that of the larger pillar 100, which is a microstructure, the pillars 104 are second nanostructures that define a horizontal dimension that is about one half that of the pillars 102.

A pattern that includes structures of different sizes may include larger structures having a cross-sectional dimension formed on a larger scale, e.g., microstructures having a cross-sectional dimension greater than about 500 nanometers in combination with smaller nanostructures. In one embodiment, microstructures of a complex nanotopography may have a cross-sectional dimension between about 500 nanometers and about 10 micrometers, between about 600 nanometers and about 1.5 micrometers, or between about 650 nanometers and about 1.2 micrometers. For example, the complex nanotopography of FIG. 5 includes micro-sized pillars 100 having a cross sectional dimension of about 1.2 micrometers.

When a pattern includes one or more larger microstructures, for instance, having a cross-sectional dimension greater than about 500 nanometers, determined either as the average cross sectional dimension of the structure or as the largest cross sectional dimension of the structure, the complex nanotopography will also include nanostructures, e.g., first nanostructures, second nanostructures of a different size and/or shape, etc. For example, pillars 102 of the complex nanotopography of FIG. 5 have a cross-sectional dimension of about 400 nanometers, and pillars 104 have a cross-sectional dimension of about 200 nanometers.

Figure 5:
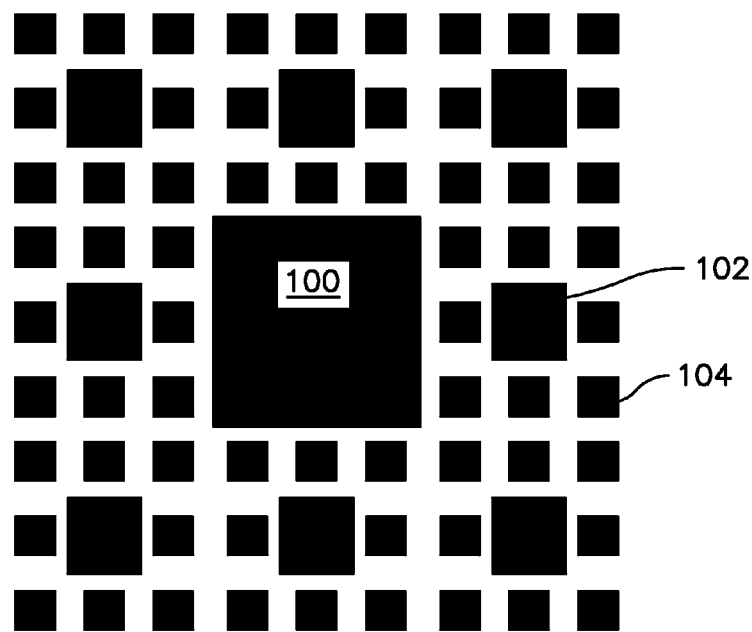
FIG. 5 illustrates one embodiment of a complex pattern that may be formed on a microneedle surface.

A nanotopography may be formed of any number of different elements. For instance, a pattern of elements may include two different elements, three different elements, an example of which is illustrated in FIG. 5, four different elements, or more. The relative proportions of the recurrence of each different element may also vary. In one embodiment, the smallest elements of a pattern will be present in larger numbers than the larger elements. For instance in the pattern of FIG. 5, there are eight pillars 104 for each pillar 102, and there are eight pillars 102 for the central large pillar 100. As elements increase in size, there may generally be fewer recurrences of the element in the nanotopography. By way of example, a first element that is about 0.5, for instance between about 0.3 and about 0.7 in cross-sectional dimension as a second, larger element may be present in the topography about five times or more than the second element. A first element that is approximately 0.25, or between about 0.15 and about 0.3 in cross-sectional dimension as a second, larger element may be present in the topography about 10 times or more than the second element.

The spacing of individual elements may also vary. For instance, center-to-center spacing of individual structures may be between about 50 nanometers and about 1 micrometer, for instance between about 100 nanometers and about 500 nanometers. For example, center-to-center spacing between structures may be on a nano-sized scale. For instance, when considering the spacing of nano-sized structures, the center-to-center spacing of the structures may be less than about 500 nanometers. This is not a requirement of a topography, however, and individual structures may be farther apart. The center-to-center spacing of structures may vary depending upon the size of the structures. For example, the ratio of the average of the cross-sectional dimensions of two adjacent structures to the center-to-center spacing between those two structures may be between about 1:1 (e.g., touching) and about 1:4, between about 1:1.5 and about 1:3.5, or between about 1:2 and about 1:3. For instance, the center to center spacing may be approximately double the average of the cross-sectional dimensions of two adjacent structures. In one embodiment, two adjacent structures each having a cross-sectional dimension of about 200 nanometers may have a center-to-center spacing of about 400 nanometers. Thus, the ratio of the average of the diameters to the center-to-center spacing in this case is 1:2.

Structure spacing may be the same, i.e., equidistant, or may vary for structures in a pattern. For instance, the smallest structures of a pattern may be spaced apart by a first distance, and the spacing between these smallest structures and a larger structure of the pattern or between two larger structures of the pattern may be the same or different as this first distance.

For example, in the pattern of FIG. 5, the smallest structures 104 have a center-to-center spacing of about 200 nanometers. The distance between the larger pillars 102 and each surrounding pillar 104 is less, about 100 nanometers. The distance between the largest pillar 100 and each surrounding pillar 104 is also less than the center-to-center spacing between to smallest pillars 104, about 100 nanometers. Of course, this is not a requirement, and all structures may be equidistant from one another or any variation in distances. In one embodiment, different structures may be in contact with one another, for instance atop one another, as discussed further below, or adjacent one another and in contact with one another.

Structures of a topography may all be formed to the same height, generally between about 10 nanometers and about 1 micrometer, but this is not a requirement, and individual structures of a pattern may vary in size in one, two, or three dimensions. In one embodiment, some or all of the structures of a topography can have a height of less than about 20 micrometers, less than about 10 micrometers, or less than about 1 micrometer, for instance less than about 750 nanometers, less than about 680 nanometers, or less than about 500 nanometers. For instance the structures can have a height between about 50 nanometers and about 20 micrometers or between about 100 nanometers and about 700 nanometers. For example, nanostructures or microstructures can have a height between about 20 nm and about 500 nm, between about 30 nm and about 300 nm, or between about 100 nm and about 200 nm, though it should be understood that structures may be nano-sized in a cross sectional dimension and may have a height that may be measured on a micro-sized scale, for instance greater than about 500 nm. Micro-sized structures can have a height that is the same or different from nano-sized structures of the same pattern. For instance, micro-sized structures can have a height of between about 500 nanometers and about 20 micrometers, or between about 1 micrometer and about 10 micrometers, in another embodiment. Micro-sized structures may also have a cross sectional dimension on a micro-scale greater than about 500 nm, and may have a height that is on a nano-sized scale of less than about 500 nm.

The aspect ratio of the structures (the ratio of the height of a structure to the cross sectional dimension of the structure) can be between about 0.15 and about 30, between about 0.2 and about 5, between about 0.5 and about 3.5, or between about 1 and about 2.5. For instance, nanostructures may have an aspect ratio falling within any of these ranges.

Figure 6:
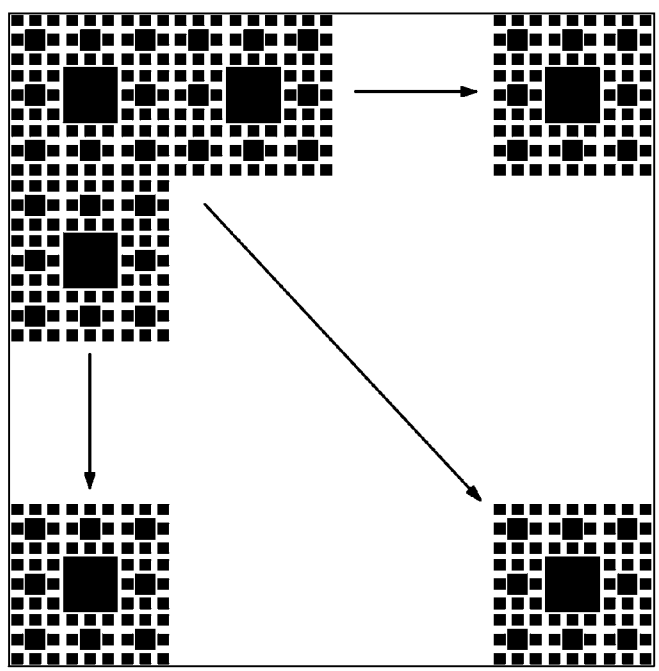
FIG. 6 illustrates a pattern including multiple iterations of the complex pattern of FIG. 5.

The microneedle surface may include a single instance of a pattern, as shown in FIG. 5, or may include multiple iterations of the same or different patterns. For example, FIG. 6 illustrates a surface pattern including the pattern of FIG. 5 in multiple iterations over a surface.

Figure 7A:
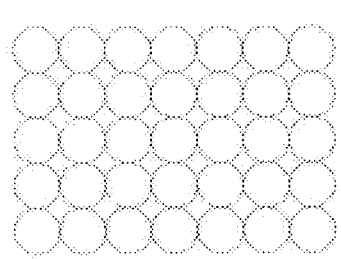
FIGS. 7A-7C illustrates exemplary packing densities as may be utilized for nano-sized structures as described herein including a square packing design (FIG. 7A), a hexagonal packing design (FIG. 7B), and a circle packing design (FIG. 7C).
Figure 7B:
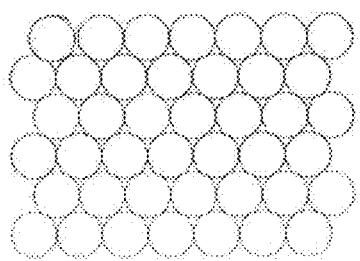
Figure 7C:
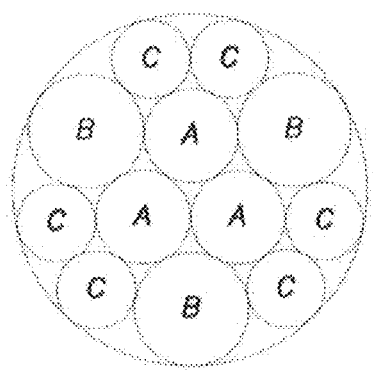

When forming the negative of the structures on the surface of a microneedle segment, the packing density of the structures may be maximized. For instance, square packing (FIG. 7A), hexagonal packing (FIG. 7B), or some variation thereof may be utilized to pattern the elements on a microneedle segment. When designing a pattern in which various sized elements of cross sectional areas A, B, and C are adjacent to one another on a microneedle surface, circle packing as indicated in FIG. 7C may be utilized. Of course, variations in packing density and determination of associated alterations in characteristics of a surface are well within the abilities of one of skill in the art. In general, center to center spacing of individual structures may be between about 50 nm and about 1 micrometer, for instance between about 100 nm and about 500 nm.

Figure 8:
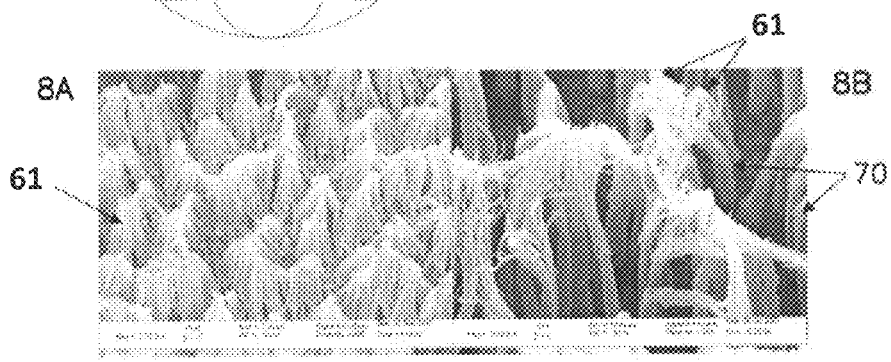
FIGS. 8A-8D illustrate complex fractal and fractal-like nanotopographies.
Figure 8:
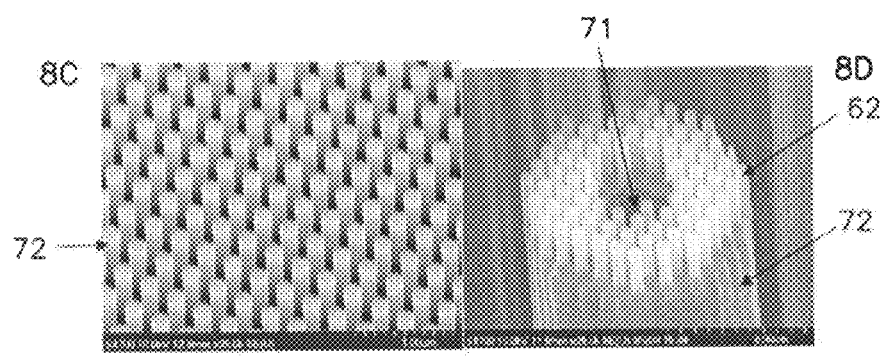

FIGS. 8A and 8B illustrate increasing magnification images of another example of a complex nanotopography. The nanotopography of FIGS. 8A and 8B includes an array of fibrous-like pillars 70 located on a substrate. At the distal end of each individual pillar, the pillar splits into multiple smaller fibers 61. At the distal end of each of these smaller fibers 61, each fiber splits again into multiple filaments (not visible in FIGS. 8A and 8B). Structures formed on a surface that have an aspect ratio greater than about 1 may be flexible, as are the structures illustrated in FIGS. 8A and 8B, or may be stiff.

FIGS. 8C and 8D illustrate another example of a complex nanotopography. In this embodiment, a plurality of pillars 72 each including an annular hollow therethrough 71 are formed on a substrate. At the distal end of each hollow pillar, a plurality of smaller pillars 62 is formed. As may be seen, the pillars of FIGS. 8C and 8D maintain their stiffness and upright orientation. Additionally, and in contrast to previous patterns, the smaller pillars 62 of this embodiment differ in shape from the larger pillars 72. Specifically, the smaller pillars 62 are not hollow, but are solid. Thus, nanotopography including structures formed to a different scale need not have all structures formed with the same shape, and structures may vary in both size and shape from the structures of a different scale.

Figure 9:
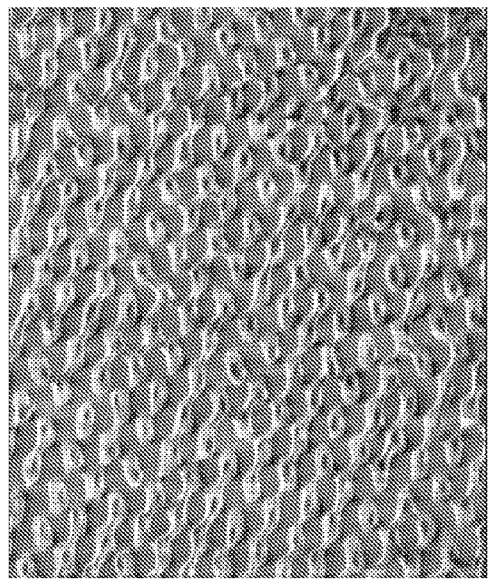
FIG. 9 illustrates another complex pattern that may be formed on a microneedle surface.

FIG. 9 illustrates another pattern including nano-sized structures as may be formed on the surface of the microneedles of an array. As may be seen, in this embodiment, individual pattern structures may be formed at the same general size, but with different orientations and shapes from one another.

Referring again to FIG. 3, a mold segment 30 may be prepared by a single-step process in which the microneedle segments 31, the negative of the nanotopography (not visible in FIG. 3) and any other structures of the microneedle mold, e.g., a channel mold 35, are formed in a single-step. Alternatively, a multi-step process may be used, in which the basic microneedle segments 31 may be pre-formed to the general shape of the microneedle portion to be formed by the segment, and then added features such as the nanotopography and a channel mold 35 may be added to the mold segment 31. Of course, a combination of processes may be utilized. For instance, the microneedle segment including the nanostructures may be formed in a single step and a mold segment may be added in a second step. According to one embodiment, a positive mold master may be first formed, which corresponds to the desired shape of the formed microneedles, and then a mold segment 31 may be formed from the positive mold master, the mold segment 31 being a negative of the positive mold master.

Any suitable material or combination thereof may be utilized in forming a mold segment including, without limitation, metals such copper, steel, nickel, aluminum, brass, and other metals, as well as thermoplastic or thermoset polymers.

A positive mold master and/or negative mold segment may be formed according to any standard microfabrication technique or combination thereof including, without limitation, lithography; etching techniques, such as wet chemical, dry, and photoresist removal; thermal oxidation of silicon; electroplating and electroless plating; diffusion processes, such as boron, phosphorus, arsenic, and antimony diffusion; ion implantation; film deposition, such as evaporation (filament, electron beam, flash, and shadowing and step coverage), sputtering, chemical vapor deposition (CVD), epitaxy (vapor phase, liquid phase, and molecular beam), electroplating, screen printing, lamination, stereolithography, laser machining, embossing molding, metal stamping, and laser ablation (including projection ablation).

An electrochemical etching process may be utilized in which electrochemical etching of solid silicon to porous silicon is used to create extremely fine (on the order of 0.01 µm) silicon networks that may be used as positive mold master structures. This method may use electrolytic anodization of silicon in aqueous hydrofluoric acid, potentially in combination with light, to etch channels into the silicon. By varying the doping concentration of the silicon wafer to be etched, the electrolytic potential during etching, the incident light intensity, and the electrolyte concentration, control over the ultimate pore structure may be achieved. The material not etched (i.e. the silicon remaining) forms the microneedles on a positive mold master.

Plasma etching may also be utilized, in which deep plasma etching of silicon is carried out to create microneedles of a positive mold master with diameters on the order of 0.1 µm or larger. Needles may be fabricated indirectly by controlling the voltage (as in electrochemical etching).

Lithography techniques, including photolithography, e-beam lithography, X-ray lithography, and so forth may be utilized for primary pattern definition and formation of a mold segment. Self-assembly technologies including phase-separated block copolymer, polymer demixing and colloidal lithography techniques may also be utilized in forming the mold segments.

Other methods as may be utilized in forming a positive mold master and/or a negative mold segment include utilization of ultra-high precision laser machining techniques, examples of which have been described by Hunt, et al. (U.S. Pat. No. 6,995,336) and Guo, et al. (U.S. Pat. No. 7,374,864), both of which are incorporated herein by reference.

A negative mold segment may be formed by laser ablation of a substrate (using, e.g., an excimer laser) to provide cavities in the shape of the desired microneedle segments. Negative mold components may also be formed by conventional photolithography, chemical etching, ion beam etching, or any other conventional processes known in the art.

The negative of the nanotopography may be formed on the surface of the mold segments or the positive nanotopography may be formed on the surface of the positive mold master according to any suitable process. The nanotopography may be formed on the entire microneedle segment surface, or only on a portion thereof. In addition, the nanotopography may extend to the surface of the supporting substrate, or may be confined to microneedles of an array, as desired.

Structure diameter, shape, and pitch may be controlled via selection of appropriate materials and methods. For example, metals may be evaporated onto colloidal-patterned substrates followed by colloidal lift-off, which generally results in prism-shaped pillars. An etching process may then be utilized to complete the structures as desired. For example, substrates patterned with colloids may be exposed to reactive ion etching (RIE, also known as dry etching) so as to refine the characteristics of a fabricated nanostructure such as nanopillar diameter, profile, height, pitch, and so forth. Wet etching may also be employed to produce alternative profiles for fabricated nanostructures initially formed according to a different process, e.g., polymer de-mixing techniques. Ordered non-spherical polymeric nanostructures may also be fabricated via temperature-controlled sintering techniques, which form a variety of ordered trigonal nanometric features in colloidal interstices following selective dissolution of polymeric nanoparticles. These and other suitable formation processes are generally known in the art (see, e.g., Wood, J R Soc Interface, 2007 Feb. 22; 4(12): 1-17, incorporated herein by reference).

Structures may be formed according to chemical addition processes. For instance, film deposition, sputtering, chemical vapor deposition (CVD), epitaxy (vapor phase, liquid phase, and molecular beam), electroplating, and so forth may be utilized for building nanostructures on a surface of a positive mold master.

Self-assembled monolayer processes as are known in the art may be utilized to form a pattern of nanostructures on a surface. For instance, the ability of block copolymers to self-organize may be used to form a monolayer pattern on a surface. The pattern may then be used as a template for the growth of desired structures, e.g., colloids, according to the pattern of the monolayer. By way of example, a two-dimensional, cross-linked polymer network may be produced from monomers with two or more reactive sites. Such cross-linked monolayers have been made using self-assembling monolayer (SAM) (e.g., a gold/alkyl thiol system) or Langmuir-Blodgett (LB) monolayer techniques (Ahmed et al., Thin Solid Films 187: 141-153 (1990)) as are known in the art. The monolayer may be crosslinked, which may lead to formation of a more structurally robust monolayer.

The monomers used to form a patterned monolayer may incorporate all the structural moieties necessary to affect the desired polymerization technique and/or monolayer formation technique, as well as to influence such properties as overall solubility, dissociation methods, and lithographic methods. A monomer may contain at least one and more often at least two, reactive functional groups.

A molecule used to form an organic monolayer may include any of various organic functional groups interspersed with chains of methylene groups. For instance a molecule may be a long chain carbon structure containing methylene chains to facilitate packing. The packing between methylene groups may allow weak Van der Waals bonding to occur, enhancing the stability of the monolayer produced and counteracting the entropic penalties associated with forming an ordered phase. In addition, different terminal moieties, such as hydrogen-bonding moieties may be present at one terminus of the molecules, in order to allow growth of structures on the formed monolayer, in which case the polymerizable chemical moieties may be placed in the middle of the chain or at the opposite terminus. Any suitable molecular recognition chemistry may be used in forming the assembly. For instance, structures may be assembled on a monolayer based on electrostatic interaction, Van der Waals interaction, metal chelation, coordination bonding (i.e., Lewis acid/base interactions), ionic bonding, covalent bonding, or hydrogen bonding.

When utilizing a SAM-based system, an additional molecule may be utilized to form the template. This additional molecule may have appropriate functionality at one of its termini in order to form a SAM. For example, on a gold surface, a terminal thiol may be included. There are a wide variety of organic molecules that may be employed to effect replication. Topochemically polymerizable moieties, such as dienes and diacetylenes, are particularly desirable as the polymerizing components. These may be interspersed with variable lengths of methylene linkers.

For an LB monolayer, only one monomer molecule is needed because the molecular recognition moiety may also serve as the polar functional group for LB formation purposes. Lithography may be carried out on a LB monolayer transferred to a substrate, or directly in the trough. For example, an LB monolayer of diacetylene monomers may be patterned by UV exposure through a mask or by electron beam patterning.

Monolayer formation may be facilitated by utilizing molecules that undergo a topochemical polymerization in the monolayer phase. By exposing the assembling film to a polymerization catalyst, a film may be grown in situ, and changed from a dynamic molecular assembly to a more robust polymerized assembly for use as a negative mold segment or a positive mold master.

Techniques useful in patterning a monolayer include, but are not limited to, photolithography, e-beam techniques, focused ion-beam techniques, and soft lithography. Various protection schemes such as photoresist may be used for a SAM-based system. Likewise, block copolymer patterns may be formed on gold and selectively etched to form patterns. For a two-component system, patterning may also be achieved with readily available techniques.

Soft lithography techniques may be utilized to pattern the monolayer in which ultraviolet light and a mask may be used for patterning. For instance, an unpatterned base monolayer may be used as a platform for assembly of a UV/particle beam reactive monomer monolayer. The monomer monolayer may then be patterned by UV photolithography, e-beam lithography, or ion beam lithography, even though the base SAM is not patterned.

Growth of structures on a patterned monolayer may be achieved by various growth mechanisms, such as through appropriate reduction chemistry of a metal salts and the use of seed or template-mediated nucleation. Using the recognition elements on the monolayer, inorganic growth may be catalyzed at this interface by a variety of methods. For instance inorganic compounds in the form of colloids bearing the shape of the patterned organic monolayer may be formed. For instance calcium carbonate or silica structures may be templated by various carbonyl functionalities such as carboxylic acids and amides. By controlling the crystal growth conditions, it is possible to control the thickness and crystal morphology of the mineral growth. Titanium dioxide may also be templated.

Templated electroless plating techniques may be used to synthesize metals using existing organic functional groups. In particular, by chelating metal atoms to the carbonyl moieties of the organic pattern, electroless metal deposition may be catalyzed on the pattern, forming patterned metallic colloids. For instance, Cu, Au, Ni, Ag, Pd, Pt and many other metals plateable by electroless plating conditions may be used to form metal structures in the shape of the organic monolayer. By controlling the electroless plating conditions, it is possible to control the thickness of the plated metal structures.

Other 'bottom-up' type growth methods as are known in the art may be utilized for forming a positive mold master and/or a mold segment including fabricated nanostructures thereon, for example a method as described in U.S. Pat. No. 7,189,435 Tuominen, et al., which is incorporated herein by reference, may be utilized. According to this method, a conducting or semiconducting substrate (for example, a metal, such as gold) may be coated with a block copolymer film (for example, a block copolymer of methylmethacrylate and styrene), where one component of the copolymer forms nanoscopic cylinders in a matrix of another component of the copolymer. A conducting layer may then be placed on top of the copolymer to form a composite structure. Upon vertically orientation of the composite structure, some of the first component may be removed, for instance by exposure to UV radiation, an electron beam, or ozone, degradation, or the like to form nanoscopic pores in that region of the second component.

In another embodiment, described in U.S. Pat. No. 6,926,953 to Nealey, et al., incorporated herein by reference, copolymer structures may be formed by exposing a substrate with an imaging layer thereon, for instance an alkylsiloxane or an octadecyltrichlorosilane self assembled monolayer, to two or more beams of selected wavelengths to form interference patterns at the imaging layer to change the wettability of the imaging layer in accordance with the interference patterns. A layer of a selected block copolymer, for instance a copolymer of polystyrene and poly(methyl methacrylate) may then be deposited onto the exposed imaging layer and annealed to separate the components of the copolymer in accordance with the pattern of wettability and to replicate the pattern of the imaging layer in the copolymer layer. Stripes or isolated regions of the separated components may thus be formed with periodic dimensions in the range of 100 nm or less.

In those embodiments in which a positive mold master is first formed, this master may be utilized to form the negative mold segments used during the injection molding process. By way of example, a negative mold segment may be prepared by an electroforming process around a positive mold master. A process of electroforming involves placing the positive mold master into an electroforming tank that deposits a metal around the features of the master. This may be any suitable metal. The metal is deposited to a desired thickness at which point the positive mold master is separated from the electroformed metal creating the negative mold components. This form of a mold is typically called an electroform. Following formation, an electroform may then be cut to fit into an injection molding apparatus.

Figure 10:
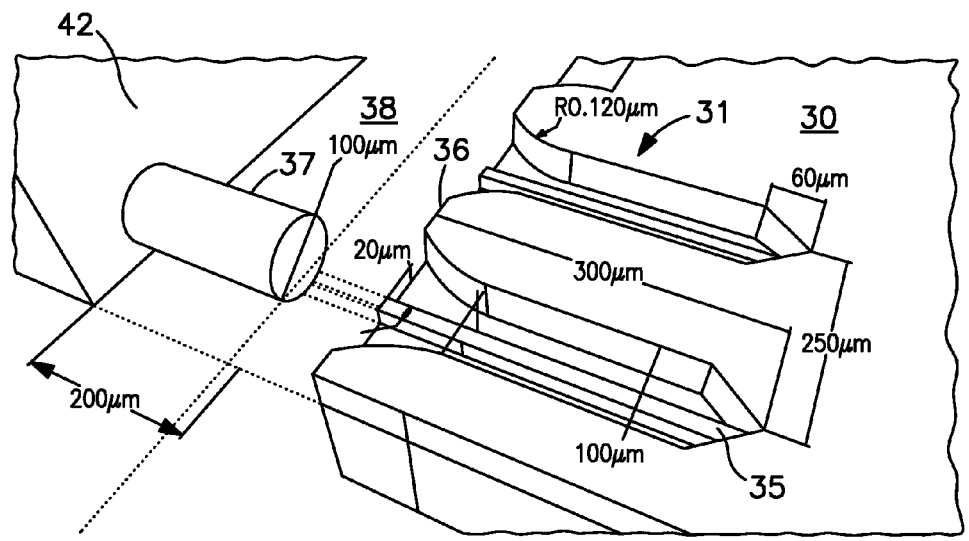
FIG. 10 schematically illustrates an injection mold segment aligned with a capping segment of a mold.

As illustrated in FIG. 10, in addition to a plurality of mold segments 30, a complete mold will also include a capping portion 42. During use, the capping portion 42 will be located in association with a mold segment 30 so as to define a substrate cavity 38 between the two. During injection molding, the substrate cavity 38 will be filled to form a substrate from which the multiple microneedles will extend. The substrate cavity may vary in thickness to meet the needs of the device, such as about 1000 micrometers or less, in some embodiments from about 1 to about 500 micrometers, and in some embodiments, from about 10 to about 200 micrometers. As shown in FIG. 10, the capping portion 42 includes an insert 37. When the complete mold is assembled, the insert 37 may contact the ends of the channel molds 35 in the microneedle segments 31. In the embodiment of FIG. 10, the capping portion 42 is otherwise unstructured, but this is not a requirement. In another embodiment a capping portion 42 may define other shapes, e.g., positive and/or negative structural features, such as grooves, slots, pins, etc., for instance for attachment of the substrate to another portion of a device such as a reservoir that contains an agent for delivery via the microneedle device.

In one embodiment, a capping portion may include a channel mold. For instance, rather than forming a channel mold 35 within a microneedle segment 31, as is shown in the illustrated embodiment, a channel mold may extend from the insert 37 of the capping portion 42. Upon alignment and assembly of the components of a mold, the channel mold of the capping portion may extend down into the center of the microneedle mold cavity, so as to form a central bore or channel in the injection molded microneedle.

When considering a hollow needle that defines a bore through the needle, the outer diameter of the needle may be between about 10 micrometers and about 100 micrometers and the inner diameter of a hollow needle may be between about 3 micrometers and about 80 micrometers.

Figure 11:
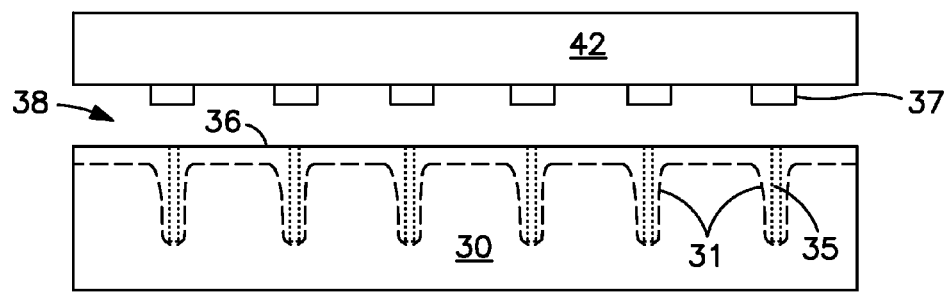
FIG. 11 schematically illustrates a cross sectional view of a mold following assembly.

FIG. 11 illustrates a side view of the mold segment 30 aligned with the capping portion 42. As may be seen, each microneedle segment 31 is aligned with an insert 37. The capping portion 42 may be lowered during assembly until each insert 37 contacts the respective channel segment 35. The substrate cavity 38 remaining between the mold segment 30 and the capping portion 42 may be utilized to mold the substrate from which the plurality of microneedles may extend.

Figure 12:
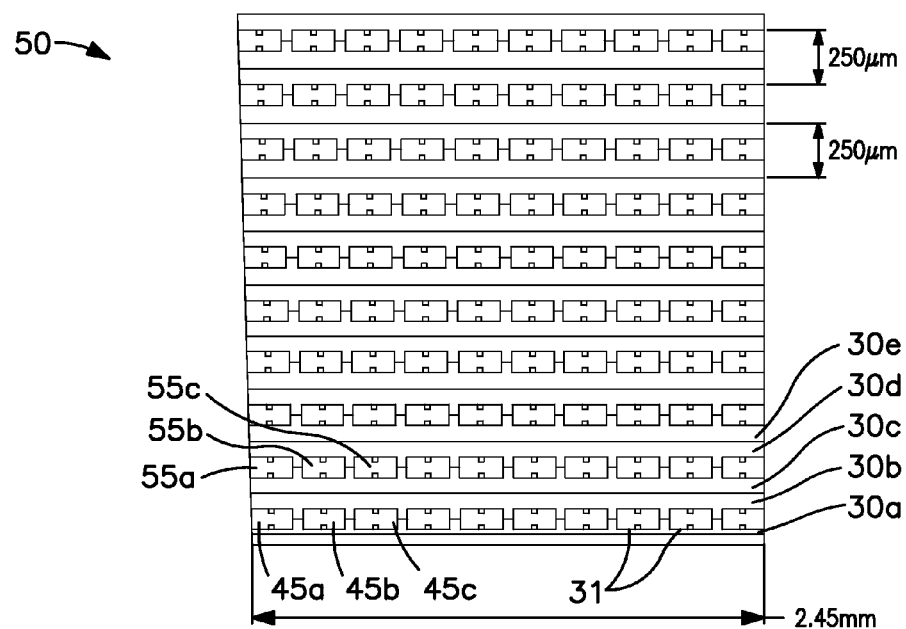
FIG. 12 schematically illustrates a top view of a microneedle array following assembly of a plurality of mold segments.

FIG. 12 illustrates a plurality of negative mold segments 30a, 30b, 30c, 30d, 30e, following alignment and assembly to form a complete 10×10 microneedle array mold 50. Each negative mold segment 30a, etc. defines multiple microneedle segments 31. A complete microneedle negative mold cavity 45a, 45b, 45c is formed by two microneedle segments 31, each of which defines a portion of the surface of a microneedle. However, it should be understood that the negative mold cavity of a single microneedle may be formed of three, four, or more individual components.

The surface of each microneedle negative mold cavity 45a, 45b, 45c, 55a, 55b, 55c will define the microneedle proper as well as the nanotopography on a surface of the microneedle and any other structures formed on the surface of the microneedles, e.g., a channel. For example, as all microneedle segments 31 define a channel mold 35, each negative mold cavity 45 may include two channel molds 35, one on each side of the mold cavity 45.

It should be understood that the number of microneedles shown in the figures is for illustrative purposes only. The actual number of microneedles formed in an injection molded array may, for example, range from about 500 to about 10,000, in some embodiments from about 2,000 to about 8,000, and in some embodiments, from about 4,000 to about 6,000.

FIG. 13 illustrates an assembled mold 60 including a single microarray mold 50 in the center. It should be understood that a single mold may include one or more microarray molds. The number of microneedle array molds on a single mold 60 can, for example, range from one to several hundred, for instance from 10 to about 500, or from about 100 to about 300.

The modular aspect of a complete mold enhances the variety of individual microneedles that may be formed in a single array. For instance, and with reference to FIG. 12, mold segments 30a, 30b may form between them negative mold cavities 45a, 45b, 45c, of a first size and/or shape. In assembling the complete microarray mold 50, mold segments 30a, 30b, 30c, 30d, 30e, etc. may be aligned with one another. Mold segments 30c, 30d may form between them negative mold cavities 55a, 55b, 55c, which may vary with regard to size, shape, features, etc. from mold cavities 45a, 45b, 45c. Accordingly a large variety of microneedles may be formed in a single array by merely mixing and matching the modular mold segments used to form the complete mold.

The various components that are assembled to form a complete mold may be formed of any suitable material or mixture of materials. Preferred materials may depend upon the material of the positive mold master (when utilized) as well as the moldable material that will be used to form the array during an injection molding process. For example, the negative mold segments 30a, 30b, etc. and the capping portion 42 may comprise a nickel material that may be formed and separated from a positive mold master.

During an injection molding process the complete mold 60 is heated, for instance to a temperature of more than about 10° C. above the softening temperature of a moldable material. In one embodiment, the mold 60 is heated to a temperature of more than about 20° C. above the softening temperature of the material to be molded prior to injection of the material. In another embodiment, the mold 60 is heated to a temperature of more than about 30° C. above the softening temperature of the material prior to injection of the material.

As utilized herein, softening temperature refers to the temperature at which a material will soften and deform when subject to ordinary forces, such as those encountered during detachment of a molded part from a mold segment. This may be conveniently measured by the Vicat softening temperature, which measures the temperature at which a flat-ended needle penetrates into a test sample (under conditions, for example, of a 50 N loading on the needle and a rate of temperature increase of 120° C./h as described in ASTM D1525-00). For amorphous materials, the softening temperature will be governed by the glass transition of the material, and in some instances the glass transition temperature will be essentially equivalent to the Vicat softening temperature. The glass transition temperature may be measured by methods known to one skilled in the art, such as by differential scanning calorimetry using a typical scanning rate of 10° C./min. For compositions comprising both crystalline and amorphous materials in which the bulk properties of the composition are governed by the crystalline material, the softening temperature is governed by the melting of the material and may be characterized by Vicat softening temperature. Examples of such materials include polypropylene, polybutylene terephthalate, polystyrene, polyethylene, polyetherimide, polyethylene terephthalate, and blends thereof.

The moldable material is also heated to a molding temperature in a chamber separate from the mold 60. The preferred temperature to which the material to be molded should be heated will generally depend on the specific material. For instance, a polymeric material may be heated to a temperature above the melting temperature such that it is molten according to standard practice.

The material to be molded according to the process may include any of a variety of materials that may be injection molded, including metals, ceramics, polymers, etc., as well as composites thereof. By way of example, silicon (e.g., liquid silicon rubber), polymers, and composites such as a polymeric binder in conjunction with a powdered metal, may be utilized. Typically, the microneedle array is formed of a biocompatible material. The term "biocompatible" generally refers to a material that does not substantially adversely affect the cells or tissues in the area where the device is to be delivered. It is also intended that the material does not cause any substantially medically undesirable effect in any other areas of the living subject. Biocompatible materials may be synthetic or natural. Some examples of suitable biocompatible materials, which are also biodegradable, include polymers of hydroxy acids such as lactic acid and glycolic acid polylactide, polyglycolide, polylactide-co-glycolide, copolymers with PEG, polyanhydrides, poly(ortho)esters, polyurethanes, poly(butyric acid), poly(valeric acid), and poly(lactide-co-caprolactone). Other suitable materials may include, without limitation, polycarbonate, polystyrene, polypropylene, polymethacrylic acid, ethylen-evinyl acetate, polytetrafluorethylene, and polyesters.

Following heating, the material is injected into the heated mold 60. The mold 60 may be heated according to any known method, for instance by use of an oil heating system that may be used to control the temperature of the components that form the cavities. In another embodiment, electromagnetic induction (EMI) heating may be used to apply rapid, localized heating to the mold 60. EMI heaters are known, and may generally include an induction coil housing containing an electromagnetic induction coil. An induction heater may be positioned close to the mold, for instance with the induction coil within about 2 mm of the mold cavity surface to provide rapid, localized heating of the surfaces of the mold cavity. During the injection molding, the temperature of the surfaces to which the polymer melt is exposed may affect the quality of the molded article, and EMI heating may be utilized to rapidly raise the surface temperature of the mold for each mold cycle.

The heated material to be molded may fill at least about 90%, for instance at least about 95%, of the volume of the mold 60. In one embodiment, the heated material may fill substantially the entire volume of the mold 60.

During the molding process, the heated material may flow to fill each successive microneedle negative mold cavity and thus fill the entire mold. The material that is molded to form the microneedle should not substantially cool before filling all of the mold cavities of the mold, since it may "skin over" or solidify in the channel prior to complete filling and block further flow of material.

Following fill of the mold, the negative mold cavities may be cooled prior to removal of the molded microneedle array. For instance, the negative mold cavities may be cooled to a temperature of less than about 5° C. below the softening temperature of the molded material prior to separating the components from one another and removing the molded array of microneedles. In another embodiment, the negative mold cavities are cooled to a temperature of less than about 10° C. below the softening temperature of the material prior to demold.

In one embodiment, the injection of the material to be molded may be performed in conjunction with a packing or injection pressure used to aid in allowing the material to fill the negative mold cavity. In one embodiment, this pressure may be greater than about 6,000 psi. In another embodiment, this pressure may be greater than about 10,000 psi. In yet another embodiment, this pressure may be greater than about 20,000 psi.

It may be desirable to add a compressive force to the material in the mold in order to assist in filling the microneedle cavities of the mold. By way of example, compressive force methods as may be utilized include those described in U.S. Pat. No. 4,489,033 to Uda, et al., U.S. Pat. No. 4,515,543 to Hamner, and U.S. Pat. No. 6,248,281 to Abe, et al., all of which are incorporated herein by reference.

According to one embodiment, ultrasonic energy may be utilized during fill of the mold, which may assist in complete filling of the microneedle cavities. For instance, ultrasonic energy may be applied to a mold cavity by means of a piezoelectric generator and an ultrasonic horn placed in conjunction with the mold. An ultrasonic horn may amplify the vibration that is generated from the piezoelectric transducer resulting in, e.g., a decrease in cavity pressure and an increase in the flow rate of material into the cavity. The forcing frequency of the ultrasonic vibration may generally be greater than about 10 kHz, or greater than about 20 kHz, in one embodiment.

A molding apparatus may include an overflow vent connected to the mold, as is generally known in the art. Molten polymeric material fed through the input line passes through the injection gate and into the mold cavity. As the polymeric material fills the mold cavity it displaces air that was in the cavity and the displaced air may escape through the overflow vent. As such, little or no displaced air becomes trapped in pockets within the mold cavity. An overflow vent serves as an exit gate to allow displaced air to leave the cavity thus allowing for more uniform filling of the mold cavity with polymeric material. The overflow vent may be positioned anywhere on the outer surface of the mold.

The cycle time of a molding process, i.e., the amount of time between injection of the material into the mold and detachment of the molded microneedle array, is generally sufficient to allow the mold to be substantially filled with material and the material to be subsequently cooled to a temperature below its softening point. The cycle time may be less than about 5 minutes, less than about 3 minutes, or less than about 90 seconds in one embodiment.

The molded array including a plurality of microneedles and a base to which the microneedles are joined may be non-porous or porous in nature, may be homogeneous or heterogeneous across the device with regard to materials, solidity, and so forth, and may have a rigid fixed or a semi-fixed shape. Beneficially, the entire array, including a substrate base, the microneedles, and any features formed on the array may be formed in a single shot injection molding step that forms a unitary construct microneedle array.

FIG. 14 is a cross sectional view of an injection molded array of microneedles following removal from a mold. In this particular embodiment, an aperture 328 is aligned with a single channel 330 via a junction 332. Alternately and as shown in other figures, a single aperture may feed two or more separate channels 330.

The channel 330 may extend from the junction 332 at the base 320 of the microneedle to the tip 322. In other embodiments, the channel 330 may not extend the full length of the microneedle 318 to the tip 322. Each microneedle 318 may include more than one channel 330, as seen in the embodiments of FIGS. 14 and 15. Alternate embodiments may include more channels if desired. The channel 330 may be variously positioned on the exterior surface, forming a substantially linear path from the base 320 towards the tip 322, or forming a winding or circuitous path along the exterior surface. In microneedles where two or more channels are present, the channels 330 may be variously spaced around the microneedle 318 in a symmetrical or asymmetrical manner.

FIG. 14 illustrates embodiments of the microneedle 318 in which the aperture 328 and channel 330 have sides that are not only coextensive with each other but may also be planar for at least some distance along the length of the pathway 326. FIG. 14 illustrates an embodiment where a single aperture 328 is aligned with more than one channel 330 on a particular microneedle 318. Other variations in geometry as are known to those of skill in the art are encompassed herein.

The addition of nanotopography on a microneedle surface may increase the surface area without a corresponding increase in volume. Increase in the surface area to volume ratio is believed to improve the interaction of a surface with surrounding biological materials. For instance, increase in the surface area to volume ratio is believed to encourage mechanical interaction between the nanotopography and surrounding proteins, e.g., extracellular matrix (ECM) proteins and/or plasma membrane proteins. As utilized herein, the term "protein" generally refers to a molecular chain of amino acids that is capable of interacting structurally, enzymatically or otherwise with other proteins, polypeptides or any other organic or inorganic molecule.

In general, the surface area to volume ratio of the microneedle array may be greater than about 10,000 cm$^{-1}$, greater than about 150,000 cm$^{-1}$, or greater than about 750,000 cm$^{-1}$. Determination of the surface area to volume ratio may be carried out according to any standard methodology as is known in the art. For instance, the specific surface area of a surface may be obtained by the physical gas adsorption method (B.E.T. method) with nitrogen as the adsorption gas, as is generally known in the art and described by Brunauer, Emmet, and Teller (J. Amer. Chem. Soc., vol. 60, Feb., 1938, pp. 309-319), incorporated herein by reference. The BET surface area may be less than about 5 m$^2$/g, in one embodiment, for instance between about 0.1 m$^2$/g and about 4.5 m$^2$/g, or between about 0.5 m$^2$/g and about 3.5 m$^2$/g. Values for surface area and volume may also be estimated from the geometry of molds used to form a surface, according to standard geometric calculations. For example, the volume may be estimated according to the calculated volume for each pattern element and the total number of pattern elements in a given area, e.g., over the surface of a single microneedle.

The nanotopography of a microneedle surface may be characterized through determination of the fractal dimension of the pattern on the microneedle. The fractal dimension is a statistical quantity that gives an indication of how completely a fractal appears to fill space as the recursive iterations continue to smaller and smaller scale. The fractal dimension of a two dimensional structure may be represented as:

$$D = \frac{\log N(e)}{\log(e)}$$

where N(e) is the number of self-similar structures needed to cover the whole object when the object is reduced by 1/e in each spatial direction.

For example, when considering the two dimensional fractal known as the Sierpenski triangle illustrated in FIG. 16, in which the mid-points of the three sides of an equilateral triangle are connected and the resulting inner triangle is removed, the fractal dimension is calculated as follows:

$$D = \frac{\log N(e)}{\log(e)}$$

$$D = \frac{\log 3}{\log 2}$$

$$D \approx 1.585$$

Thus, the Sierpenski triangle fractal exhibits an increase in line length over the initial two dimensional equilateral triangle. Additionally, this increase in line length is not accompanied by a corresponding increase in area.

The fractal dimension of the pattern illustrated in FIG. 5 is approximately 1.84. In one embodiment, nanotopography of a surface of the device may exhibit a fractal dimension of greater than about 1, for instance between about 1.2 and about 5, between about 1.5 and about 3, or between about 1.5 and about 2.5.

In addition to or alternative to the examination of surface area to volume ratio and/or fractal dimension, a microneedle surface including a fabricated nanotopography thereon may be characterized by other methods including, without limitation, surface roughness, elastic modulus, surface energy, and so forth.

Methods for determining surface roughness are generally known in the art. For instance, an atomic force microscope process in contact or non-contact mode may be utilized according to standard practice to determine the surface roughness of a material. Surface roughness that may be utilized to characterize a microneedle may include the average roughness ($R_A$), the root mean square roughness, the skewness, and/or the kurtosis. In general, the average surface roughness (i.e., the arithmetical mean height of the surface are roughness parameter as defined in the ISO 25178 series) of a surface defining a fabricated nanotopography thereon may be less than about 200 nanometers, less than about 190 nanometers, less than about 100 nanometers, or less than about 50 nanometers. For instance, the average surface roughness may be between about 10 nanometers and about 200 nanometers, or between about 50 nanometers and about 190 nanometers The microneedles may be characterized by the elastic modulus of the nanopatterned surface, for instance by the change in elastic modulus upon the addition of a nanotopography to a surface. In general, the addition of a plurality of structures forming nanotopography on a surface may decrease the elastic modulus of a material, as the addition of nano-sized structures on a surface will lead to a reduction in continuity of the surface and a related change in surface area. As compared to a similar surface formed according to the same injection molding process and of the same materials, but for a pattern of nanotopography on the surface, the device including nanotopography thereon may exhibit a decrease in elastic modulus of between about 35% and about 99%, for instance between about 50% and about 99%, or between about 75% and about 80%. By way of example, the effective compression modulus of a nanopatterned surface may be less than about 50 MPa, or less than about 20 MPa. In one embodiment the effective compression modulus may be between about 0.2 MPa and about 50 MPa, between about 5 MPa and about 35 MPa, or between about 10 MPa and about 20 MPa. The effective shear modulus may be less than about 320 MPa, or less than about 220 MPa. For instance, the effective shear modulus may be between about 4 MPa and about 320 MPa, or between about 50 MPa and about 250 MPa, in one embodiment.

The microneedle including nanotopography thereon may also exhibit an increase in surface energy as compared to a similar microneedle that does not have a surface defining a pattern of nanotopography thereon. For instance, a microneedle including a nanotopography formed thereon may exhibit an increase in surface energy as compared to a similar microneedle of the same materials and formed according to the same injection molding methods, but for the inclusion of a pattern of nanotopography on a surface. For instance, the water contact angle of a surface including a nanotopography thereon may be greater than about 80°, greater than about 90°, greater than about 100°, or greater than about 110°. For example, the water contact angle of a surface may be between about 80° and about 150°, between about 90° and about 130°, or between about 100° and about 120°, in one embodiment.

The microneedle array may be used for interaction with tissue, such as in delivery of a bioactive agent to a cell. For example, the microneedle array may be a component of a transdermal patch used to deliver an agent to the tissue or to one or more cell types of the tissue, for structural support of a tissue, for removal of a portion or component of the tissue, and so forth. The microneedle array may be used in one embodiment for transport of a substance across one or more layers of the skin.

During use, the microneedles of the array may interact with surrounding biological components and regulate or modulate (i.e., change) intracellular and/or intercellular signal transduction associated with cell/cell interactions, endocytosis, inflammatory response, and so forth. For instance, through interaction between the nanotopography on a surface of the microneedles and surrounding biological materials or structures, the device may regulate and/or modulate membrane potential, membrane proteins, and/or intercellular junctions (e.g., tight junctions, gap junctions, and/or desmasomes). The microneedle array may be utilized for transdermal delivery of agents or withdrawal of materials across biological barriers such as the skin, the blood-brain barrier, mucosal tissues, blood and lymph vessels, and so forth without instigating a foreign body or immune response.

Structures of the nanotopography may mimic and/or interact with one or more ECM protein such as collagen, laminin, fibronectin, etc. Cells in the local area surrounding the microneedles may maintain an anti-inflammatory microenvironment as the microneedle surfaces may better mimic the local environment either directly or indirectly, e.g., due to protein adsorption at the surface. Thus, materials may be delivered by use of the device without development of a foreign body or immune response.

In one embodiment, the microneedles of an array may interact with one or more components of the contacting epithelial tissue to increase porosity of the tissue via paracellular and/or transcellular transport mechanisms. Epithelial tissue as may be rendered more porous by use of a microneedle array may include both simple and stratified epithelium, including both keratinized epithelium and transitional epithelium. Epithelial tissue encompassed herein may include any cell types of an epithelial layer including, without limitation, keratinocytes, squamous cells, columnar cells, cuboidal cells and pseudostratified cells.

Interaction of the microneedles with components of a cell network or layer of the epidermis may modulate (i.e., change) the structure of intercellular junctions therein. An intracellular junction may be at least one junction selected from the group consisting of tight junctions, gap junctions, and desmasomes. By way of example, interaction between biological components and structures of nanotopography may modulate proteins of a cellular network so as to induce the opening of tight junctions of the stratum granulosum, thereby providing improved delivery of an active agent across the epidermis, and in one particular embodiment, a high molecular weight active agent. Tight junctions have been found in the stratum granulosum and opening of the tight junctions may provide a paracellular route for improved delivery of active agents, particularly large molecular weight active agents and/or agents that exhibit low lipophilicity that have previously been blocked from transdermal delivery.

Due to improved interaction with surrounding biological components, the devices may facilitate improved uptake of a delivered agent. For example, the pharmacokinetic (PK) profile (i.e., the profile of absorption through the epithelial membranes) of a protein therapeutic may be enhanced through utilization of a device including a pattern of nanotopography. By way of example, a protein therapeutic having a molecular weight of over 100 kDa, for instance between about 100 kDa and about 200 kDa, or about 150 kDa, may be delivered transdermally via a patch including an injection molded microneedle array. In one embodiment, a patch may be utilized to deliver a single dose of the protein therapeutic, for instance between about 200 and about 500 µL, or about 250 µL. Following attachment of the transdermal patch to the skin, the recipient may exhibit a PK profile that reflects a rapid rise in blood serum concentration up to between about 500 and about 1000 nanograms therapeutic per milliliter per square centimeter of patch area, for instance between about 750 and about 850 nanograms therapeutic per milliliter per square centimeter patch area, within about 1 to about 4 hours of administration. This initial rapid rise in blood serum level, which reflects rapid uptake of the therapeutic across the dermal barrier, may be followed by a less rapid decline of blood serum concentration over between about 20 and about 30 hours, for instance over about 24 hours, down to a negligible blood serum concentration of the therapeutic. Moreover, the rapid uptake of the delivered therapeutic may be accompanied by little or no inflammation. Specifically, in addition to promoting improved delivery of an agent across a transdermal barrier, the devices may also limit foreign body response and other undesirable reactions, such as inflammation. Use of previously known devices, such as transdermal patches with no nanotopography defined at the skin contacting surface, often led to local areas of inflammation and irritation.

The surface of a microneedle including fabricated nanotopography thereon may be functionalized for improved interaction with tissues or individual cells during use. For instance, one or more biomolecules such as polynucleotides, polypeptides, entire proteins, polysaccharides, and the like may be bound to a structured surface prior to use.

In some embodiments, a surface including structures formed thereon may already contain suitable reactivity such that additional desired functionality may spontaneously attach to the surface with no pretreatment of the surface necessary. However, in other embodiments, pretreatment of the structured surface prior to attachment of the desired compound may be carried out. For instance, reactivity of a structure surface may be increased through addition or creation of amine, carboxylic acid, hydroxy, aldehyde, thiol, or ester groups on the surface. In one representative embodiment, a microneedle surface including a pattern of nanostructures formed thereon may be aminated through contact with an amine-containing compound such as 3-aminopropyltriethoxy silane in order to increase the amine functionality of the surface and bind one or more biomolecules to the surface via the added amine functionality.

Materials as may be desirably bound to the surface of a microneedle array may include ECM proteins such as laminins, tropoelastin and/or elastin, tropocollagen and/or collagen, fibronectin, and the like. Short polypeptide fragments may be bound to the surface of a patterned device such as an RGD sequence, which is part of the recognition sequence of integrin binding to many ECM proteins. Thus, functionalization of a microneedle surface with RGD may encourage interaction of the device with ECM proteins and further limit foreign body response to the device during use.

An injected molded microneedle array may be associated with an agent for delivery via the microneedle array. For instance, a transdermal microneedle patch may be utilized for delivery of materials beneath the stratum corneum to the stratum spinosum or the stratum germinativum, or even deeper into the dermis. In general, an agent may be transported across the stratum corneum in conjunction with the microneedle, e.g., within the microneedle or at the surface of the microneedle.

The device may include a reservoir, e.g., a vessel, a porous matrix, etc., that may store and agent and provide the agent for delivery. The device may include a reservoir within the device itself. For instance, the device may include a hollow, or multiple pores that may carry one or more agents for delivery. The agent may be released from the device via degradation of a portion or the entire device or via diffusion of the agent from the device.

Figure 17A:
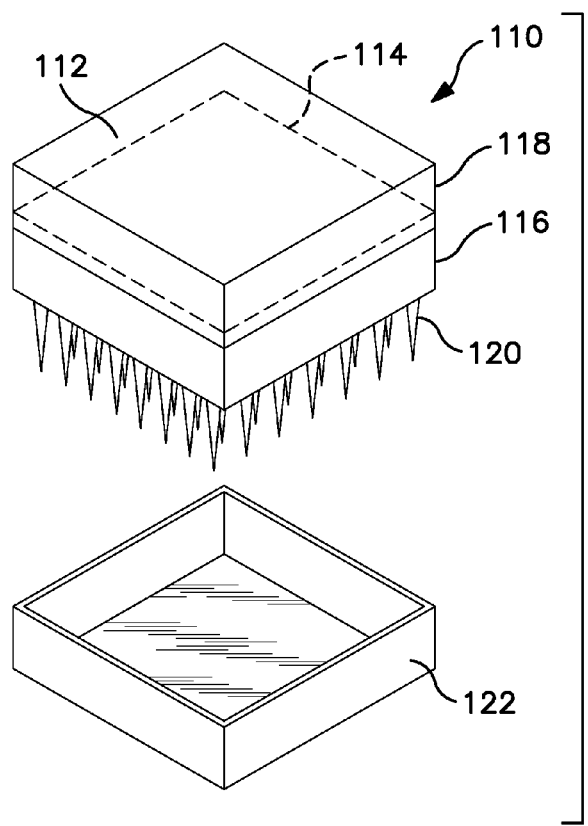
FIGS. 17A and 17B schematically illustrate one embodiment of a device in an exploded view (FIG. 17A) and assembled (FIG. 17B).
Figure 17B:
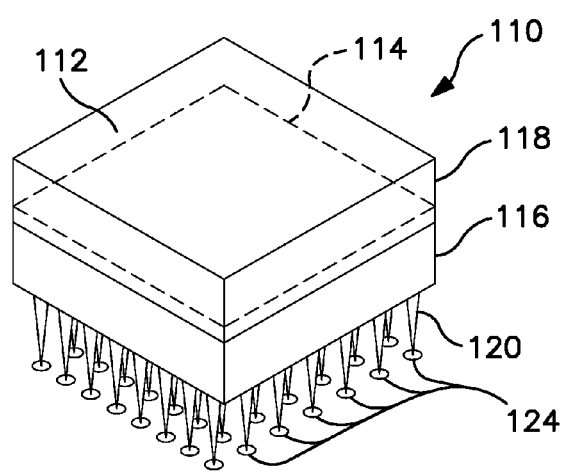

FIGS. 17A and 17B are perspective views of a device including a reservoir. The device 110 includes a reservoir 112 defined by an impermeable backing layer 114 and a microneedle array 116. The backing layer and the microneedle array 116 are joined together about the outer periphery of the device, as indicated at 118. The impermeable backing layer 114 may be joined by an adhesive, a heat seal or the like. The device 110 also includes a plurality of microneedles 120. A release liner 122 may be removed prior to use of the device to expose microneedles 120.

A formulation including one or more agents may be retained within the reservoir 112. Materials suitable for use as impermeable backing layer 114 may include materials such as polyesters, polyethylene, polypropylene and other synthetic polymers. The material is generally heat or otherwise sealable to the backing layer to provide a barrier to transverse flow of reservoir contents.

Reservoir 112, defined by the space or gap between the impermeable backing layer 114 and the base of the microneedle array 116, provides a storage structure in which to retain the suspension of agents to be administered. The reservoir may be formed from a variety of materials that are compatible with an agent to be contained therein. By way of example, natural and synthetic polymers, metals, ceramics, semiconductor materials, and composites thereof may form the reservoir.

In one embodiment, the reservoir may be attached to the base upon which the microneedles are located. According to another embodiment, the reservoir may be separate and removably connectable to the microneedle array or in fluid communication with the microneedle array, for instance via appropriate tubing, leur locks, etc.

The device may include one or a plurality of reservoirs for storing agents to be delivered. For instance, the device may include a single reservoir that stores a single or a multiple agent-containing formulation, or the device may include multiple reservoirs, each of which stores one or more agents for delivery to all or a portion of the array of microneedles. Multiple reservoirs may each store a different material that may be combined for delivery. For instance, a first reservoir may contain an agent, e.g., a drug, and a second reservoir may contain a vehicle, e.g., saline. The different agents may be mixed prior to delivery. Mixing may be triggered by any means, including, for example, mechanical disruption (i.e. puncturing, degradation, or breaking), changing the porosity, or electrochemical degradation of the walls or membranes separating the chambers. Multiple reservoirs may contain different active agents for delivery that may be delivered in conjunction with one another or sequentially.

In one embodiment, the reservoir may be in fluid communication with one or more microneedles of the transdermal device, and the microneedles may define a structure (e.g., a central or lateral bore) to allow transport of delivered agents beneath the barrier layer.

Figure 18:
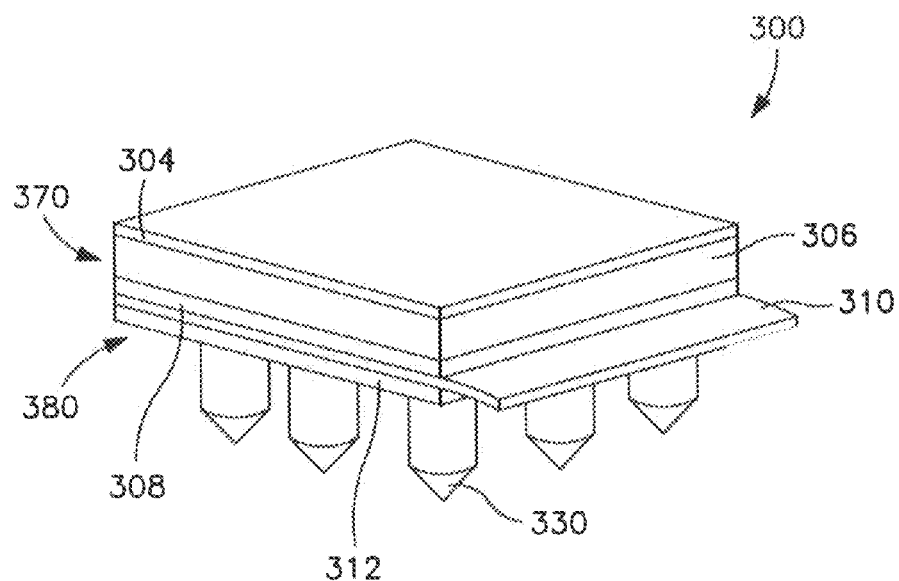
FIG. 18 is a perspective view of one embodiment of a transdermal patch prior to delivery of a drug compound.
Figure 19:
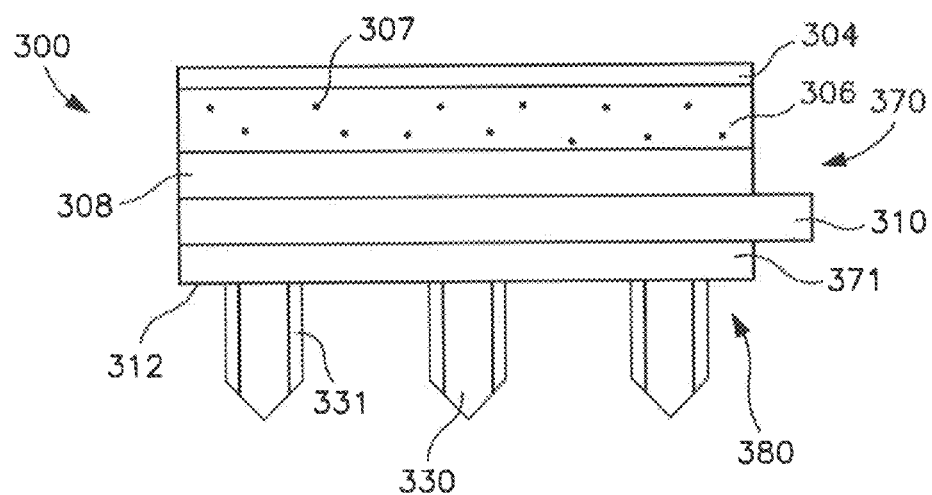
FIG. 19 is a front view of the patch of FIG. 18.

In alternative embodiments, a device may include a microneedle assembly and a reservoir assembly with flow prevention between the two prior to use. For instance, a device may include a release member positioned adjacent to both a reservoir and a microneedle array. The release member may be separated from the device prior to use such that during use the reservoir and the microneedle array are in fluid communication with one another. Separation may be accomplished through the partial or complete detachment of the release member. For example, referring to FIGS. 18-23, one embodiment of a release member is shown that is configured to be detached from a transdermal patch to initiate the flow of a drug compound. More particularly, FIGS. 18-19 show a transdermal patch 300 that contains a drug delivery assembly 370 and a microneedle assembly 380. The drug delivery assembly 370 includes a reservoir 306 positioned adjacent to a rate control membrane 308.

The rate control membrane may help slow down the flow rate of the drug compound upon its release. Specifically, fluidic drug compounds passing from the drug reservoir to the microneedle assembly via microfluidic channels may experience a drop in pressure that results in a reduction in flow rate. If this difference is too great, some backpressure may be created that may impede the flow of the compound and potentially overcome the capillary pressure of the fluid through the microfluidic channels. Thus, the use of the rate control membrane may ameliorate this difference in pressure and allow the drug compound to be introduced into the microneedle at a more controlled flow rate. The particular materials, thickness, etc. of the rate control membrane may vary based on multiple factors, such as the viscosity of the drug compound, the desired delivery time, etc.

The rate control membrane may be fabricated from permeable, semi-permeable or microporous materials that are known in the art to control the rate of drug compounds and having permeability to the permeation enhancer lower than that of drug reservoir. For example, the material used to form the rate control membrane may have an average pore size of from about 50 nm to about 5 micrometers, in some embodiments from about 100 nm to about 2 micrometers, and in some embodiments, from about 300 nm to about 1 micrometer (e.g., about 600 nm). Suitable membrane materials include, for instance, fibrous webs (e.g., woven or nonwoven), apertured films, foams, sponges, etc., which are formed from polymers such as polyethylene, polypropylene, polyvinyl acetate, ethylene n-butyl acetate and ethylene vinyl acetate copolymers. Such membrane materials are also described in more detail in U.S. Pat. Nos. 3,797,494, 4,031,894, 4,201,211, 4,379,454, 4,436,741, 4,588,580, 4,615,699, 4,661,105, 4,681,584, 4,698,062, 4,725,272, 4,832,953, 4,908,027, 5,004,610, 5,310,559, 5,342,623, 5,344,656, 5,364,630, and 6,375,978, which are incorporated in their entirety herein by reference for all relevant purposes. A particularly suitable membrane material is available from Lohmann Therapie-Systeme.

Referring to FIGS. 18-19, although optional, the assembly 370 also contains an adhesive layer 304 that is positioned adjacent to the reservoir 306. The microneedle assembly 380 likewise includes a support 312 from which extends a plurality of microneedles 330 having channels 331, such as described above. The layers of the drug delivery assembly 370 and/or the microneedle assembly 380 may be attached together if desired using any known bonding technique, such as through adhesive bonding, thermal bonding, ultrasonic bonding, etc.

Regardless of the particular configuration employed, the patch 300 also contains a release member 310 that is positioned between the drug delivery assembly 370 and the microneedle assembly 380. While the release member 310 may optionally be bonded to the adjacent support 312 and/or rate control membrane 308, it is typically desired that it is only lightly bonded, if at all, so that the release member 310 may be easily withdrawn from the patch 300. If desired, the release member 310 may also contain a tab portion 371 (FIGS. 18-19) that extends at least partly beyond the perimeter of the patch 300 to facilitate the ability of a user to grab onto the member and pull it in the desired direction. In its "inactive" configuration as shown in FIGS. 18-19, the drug delivery assembly 370 of the patch 300 securely retains a drug compound 307 so that it does not flow to any significant extent into the microneedles 330. The patch may be "activated" by simply applying a force to the release member so that it is detached from the patch.

Figure 20:
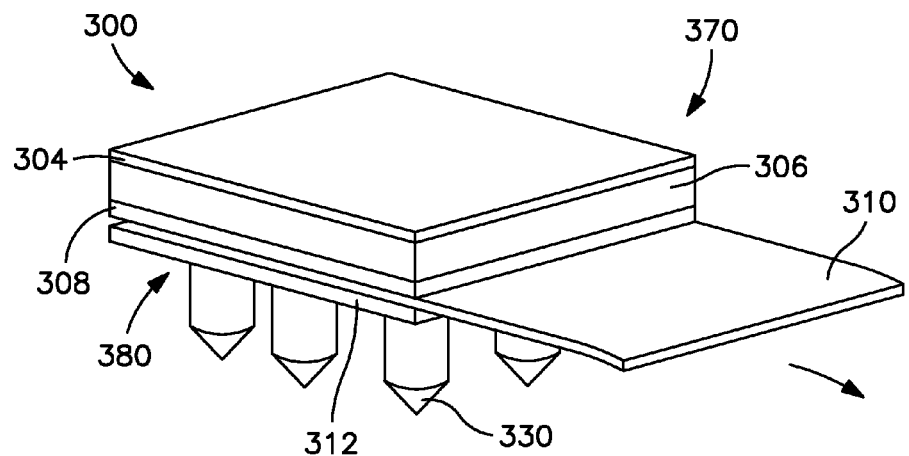
FIG. 20 is a perspective view of the patch of FIG. 18 in which the release member is partially withdrawn from the patch.
Figure 21:
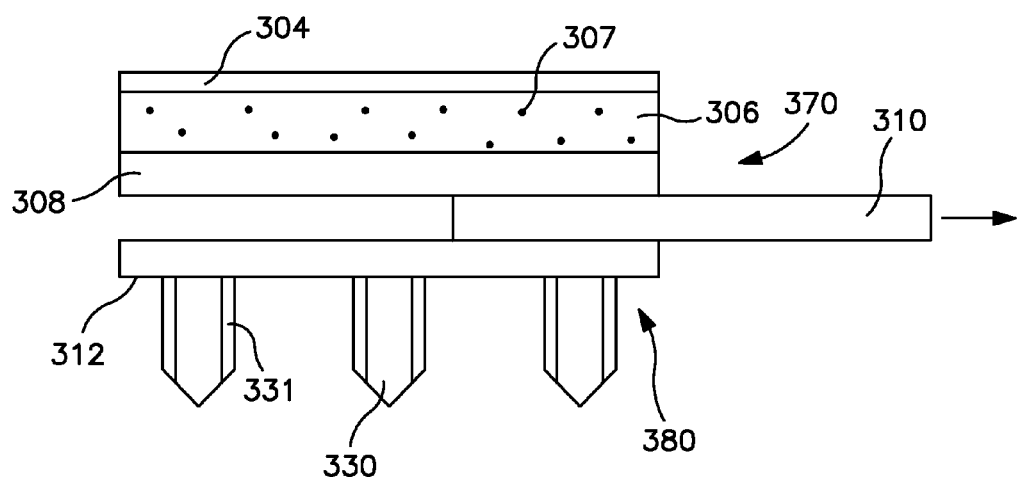
FIG. 21 is a front view of the patch of FIG. 20.
Figure 22:
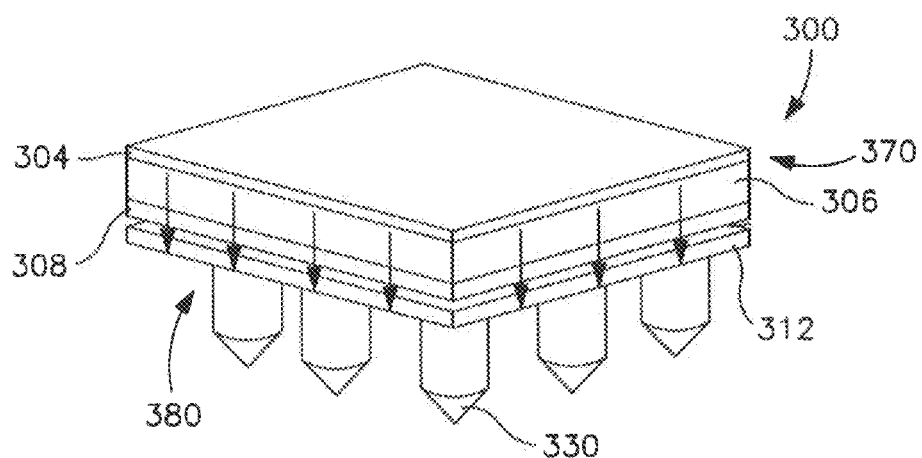
FIG. 22 is a perspective view of the transdermal patch of FIG. 18 after removal of the release member and during use.
Figure 23:
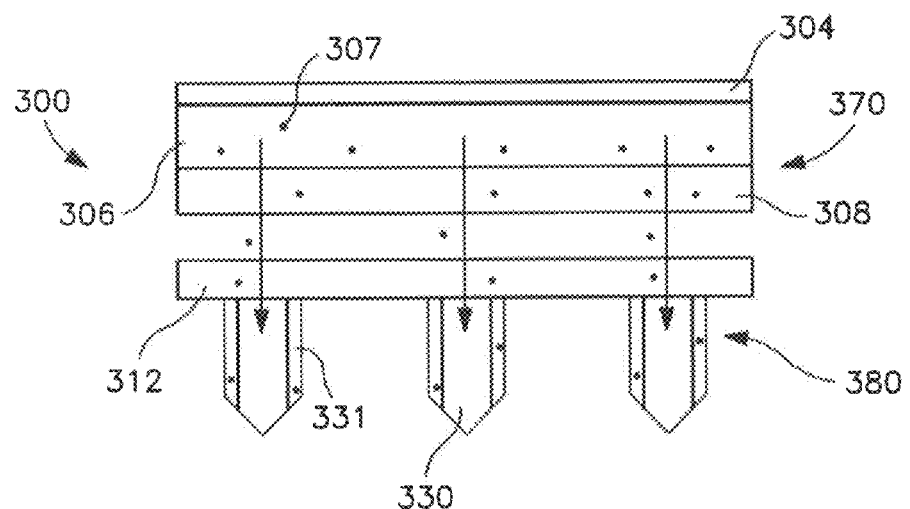
FIG. 23 is a front view of the patch of FIG. 22.

Referring to FIGS. 20-21, one embodiment for activating the patch 300 is shown in which the release member 310 is pulled in a longitudinal direction. The entire release member 310 may be removed as shown in FIGS. 22-23, or it may simply be partially detached as shown in FIGS. 20-21. In either case, however, the seal previously formed between the release member 310 and the aperture (not shown) of the support 312 is broken. In this manner, a drug compound 107 may begin to flow from the drug delivery assembly 170 and into the channels 131 of the microneedles 130 via the support 112. An exemplary illustration of how the drug compound 307 flows from the reservoir 306 and into the channels 331 is shown in FIGS. 22-23. Notably, the flow of the drug compound 307 is passively initiated and does not require any active displacement mechanisms (e.g., pumps).

In the embodiments shown in FIGS. 18-23, the detachment of the release member immediately initiates the flow of the drug compound to the microneedles because the drug delivery assembly is already disposed in fluid communication with the microneedle assembly. In certain embodiments, however, it may be desired to provide the user with a greater degree of control over the timing of the release of the drug compound. This may be accomplished by using a patch configuration in which the microneedle assembly is not initially in fluid communication with the drug delivery assembly. When it is desired to use the patch, the user may physically manipulate the two separate assemblies into fluid communication. The release member may be separated either before or after such physical manipulation occurs.

Figure 24:
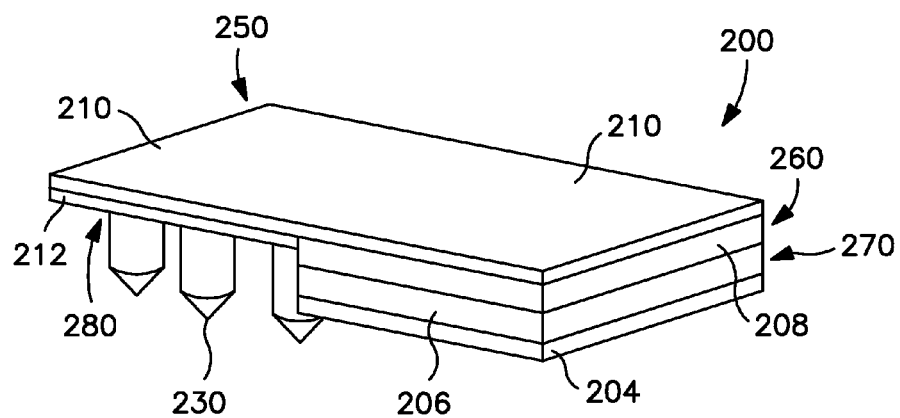
FIG. 24 is a perspective view of another embodiment of a transdermal patch prior to delivery of a drug compound.
Figure 25:
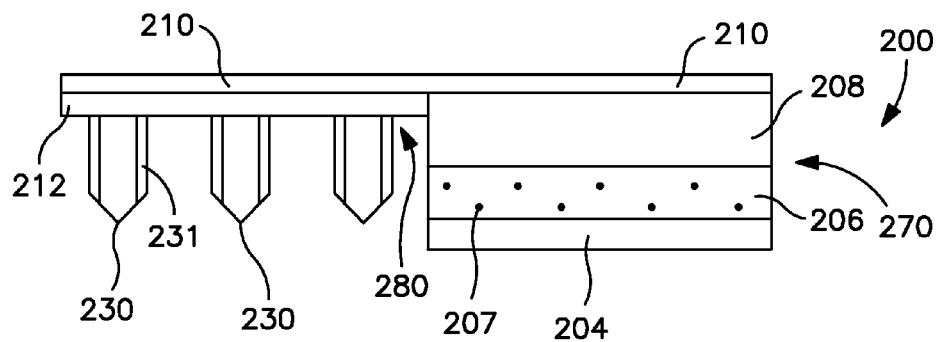
FIG. 25 is a front view of the patch of FIG. 24.

Referring to FIGS. 24-29, for example, one particular embodiment of a patch 200 is shown. FIGS. 24-25 illustrate the patch 200 before use, and shows a first section 250 formed by a microneedle assembly 280 and a second section 260 formed by a drug delivery assembly 270. The drug delivery assembly 270 includes a reservoir 206 positioned adjacent to a rate control membrane 208 as described above. Although optional, the assembly 270 also contains an adhesive layer 204 that is positioned adjacent to the reservoir 206. The microneedle assembly 280 likewise includes a support 212 from which extends a plurality of microneedles 230 having channels 231, such as described above.

Figure 26:
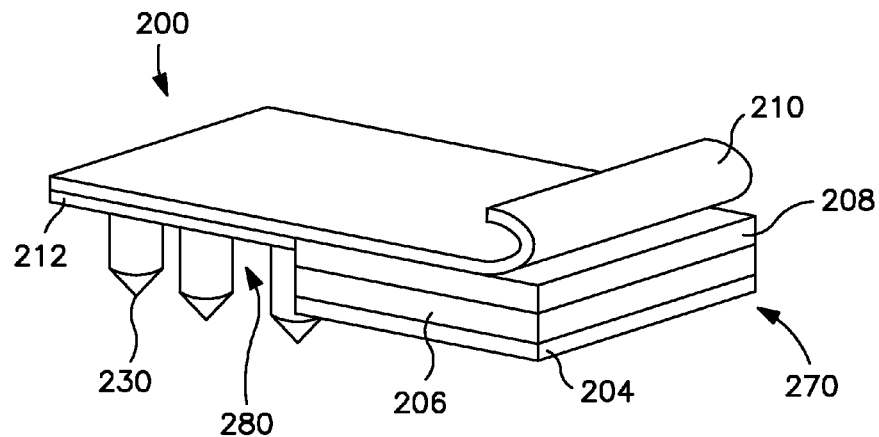
FIG. 26 is a perspective view of the patch of FIG. 24 in which the release member is partially peeled away from the patch.
Figure 27:
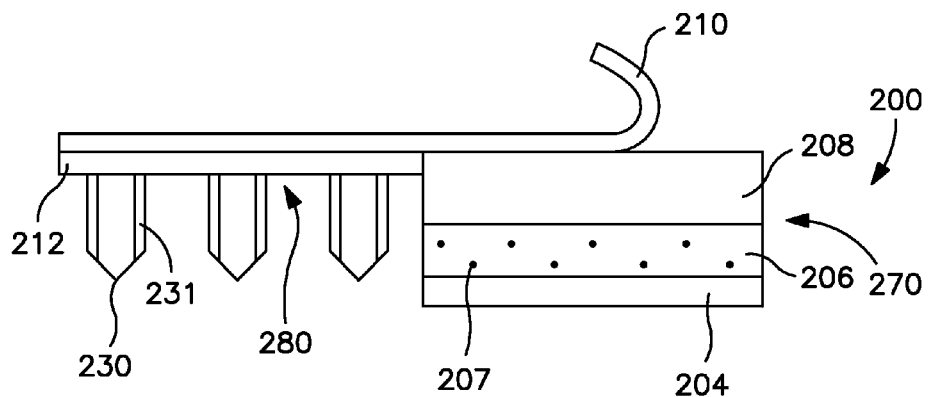
FIG. 27 is a front view of the patch of FIG. 26.
Figure 28:
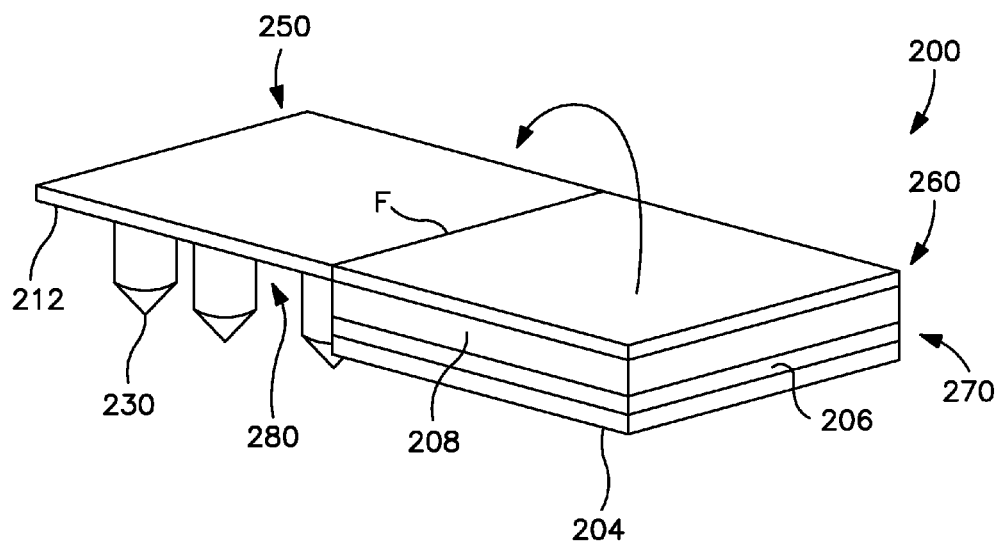
FIG. 28 is a perspective view of the patch of FIG. 24 in which the release member is completely peeled away from the patch.
Figure 29:
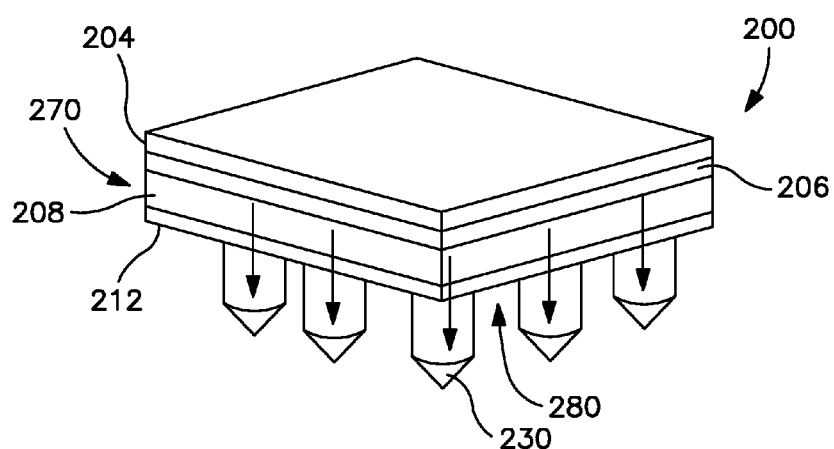
FIG. 29 is a perspective view of the transdermal patch of FIG. 24 after removal of the release member and during use.
Figure 32A:
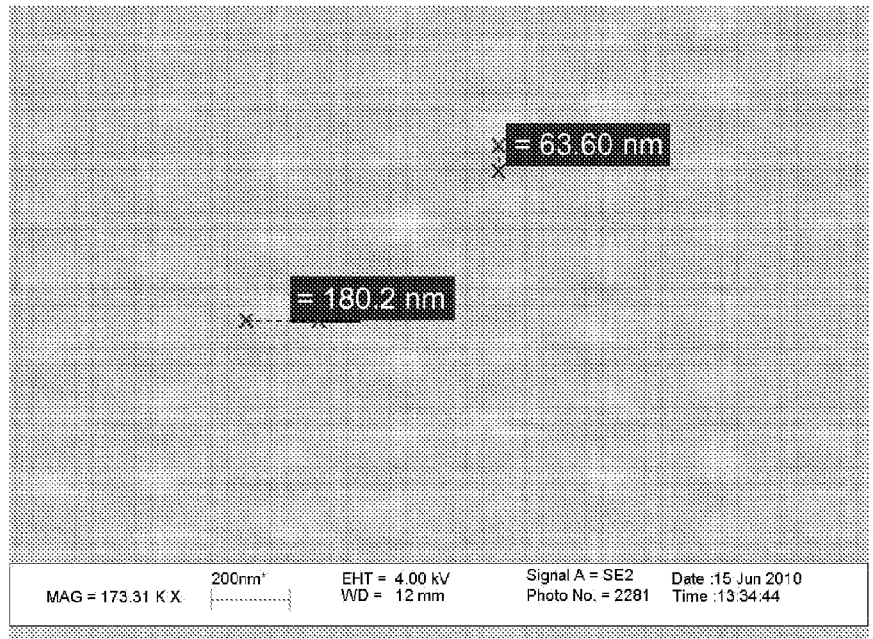
FIGS. 32A and 32B are two SEM of a film including another nanopatterned surface.
Figure 32B:
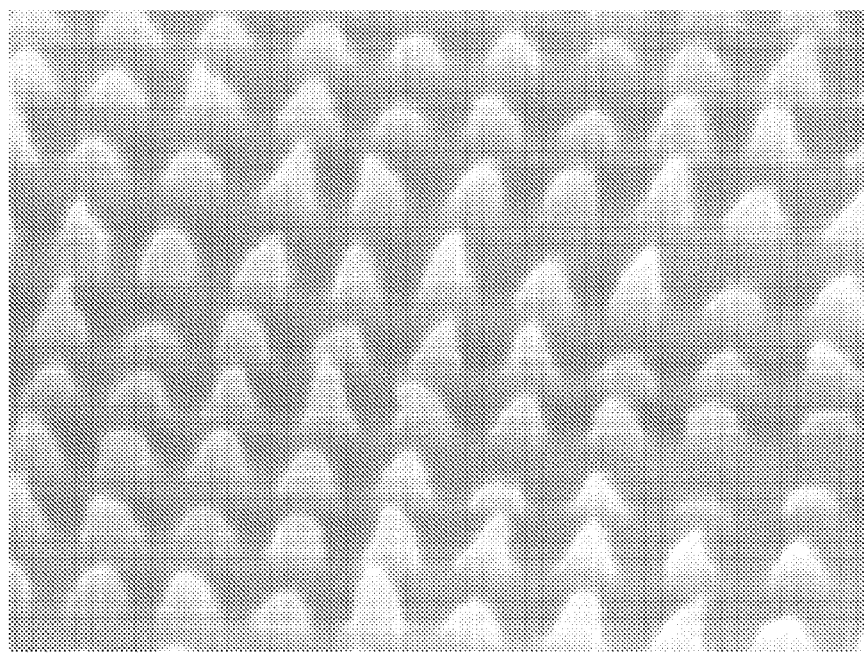
Figure 33:
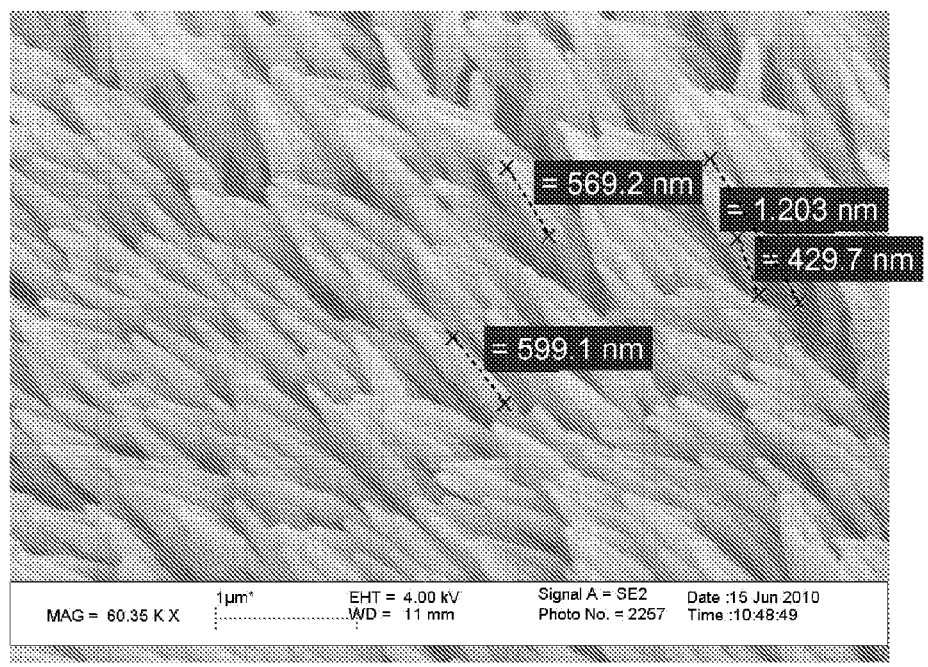
FIG. 33 is an SEM of a film including another nanopatterned surface.
Figure 34:
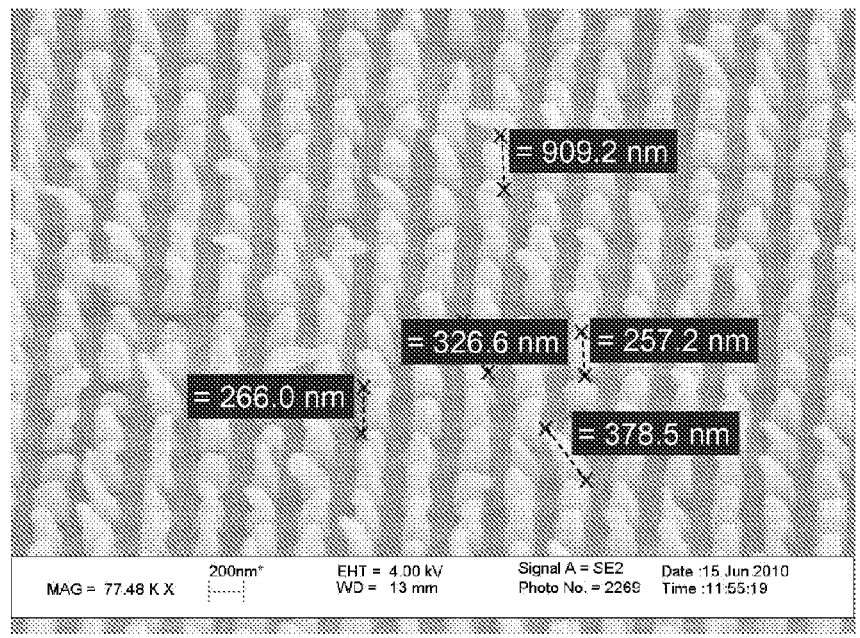
FIG. 34 is an SEM of a film including another nanopatterned surface.
Figure 35:
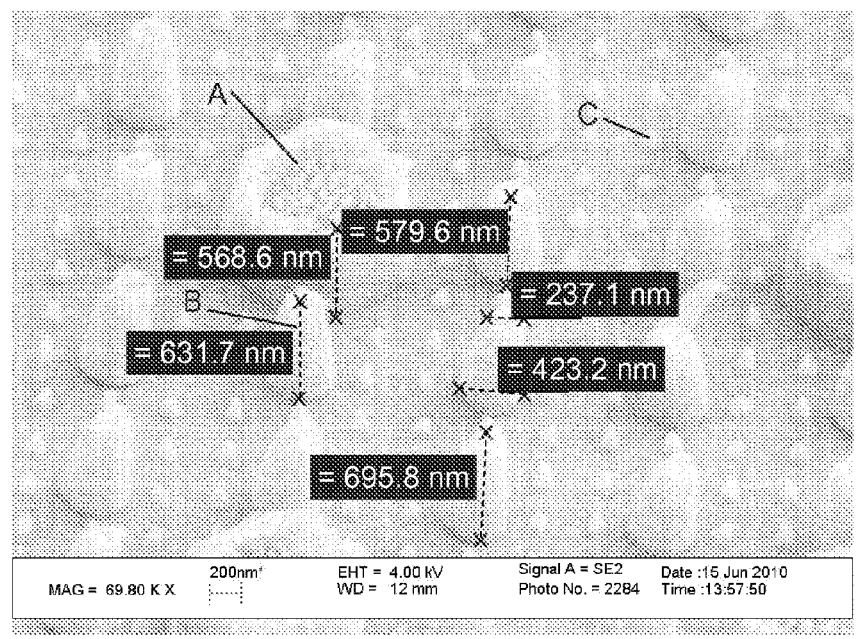
FIG. 35 is an SEM of a film including another nanopatterned surface.
Figure 36:
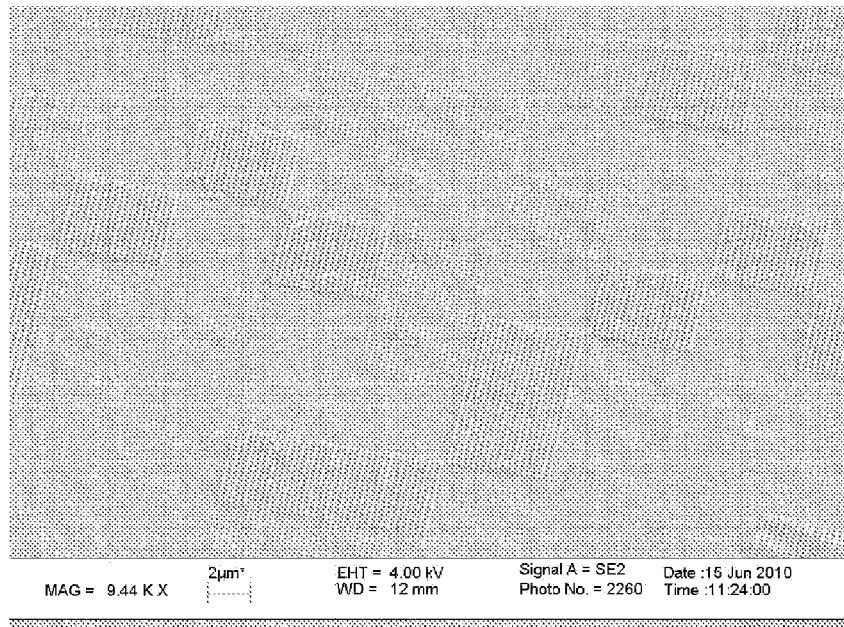
FIG. 36 is an SEM of a film including another nanopatterned surface.
Figure 37:
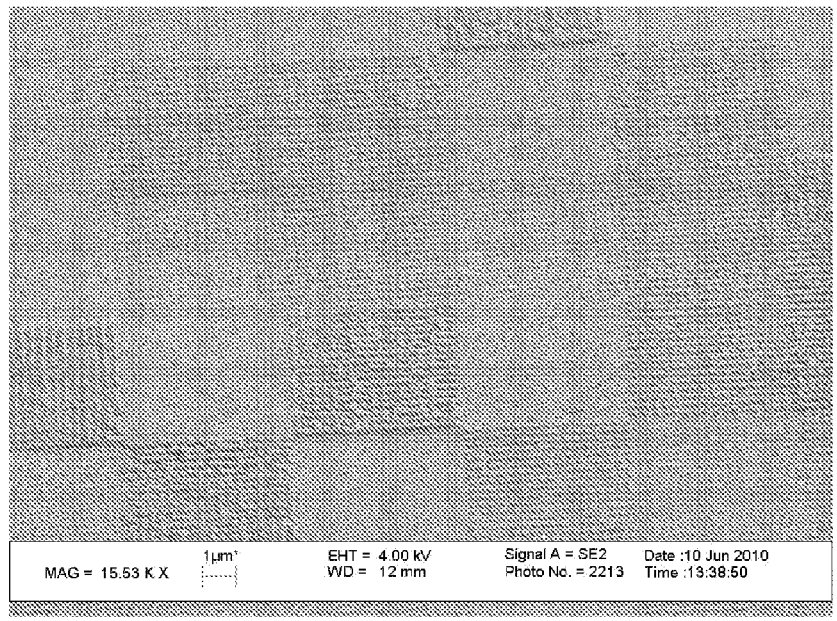
FIG. 37 is an SEM of a film including another nanopatterned surface.
Figure 38:
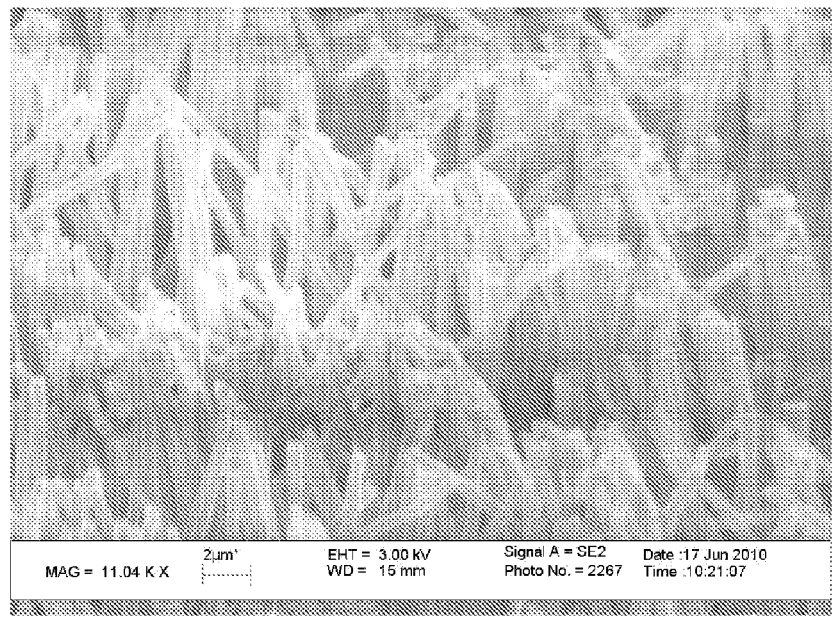
FIG. 38 is an SEM of a film including another nanopatterned surface.
Figure 39:
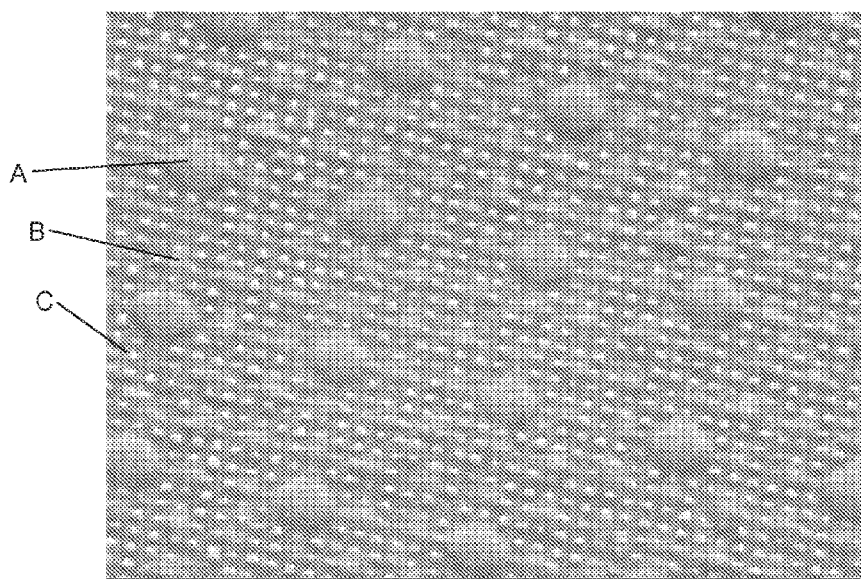
FIG. 39 is an SEM of a film including another nanopatterned surface.

In this embodiment, the support 212 and the rate control membrane 208 are initially positioned horizontally adjacent to each other, and a release member 210 extends over the support 212 and the rate control member 208. In this particular embodiment, it is generally desired that the release member 210 is releasably attached to the support 212 and the rate control membrane 208 with an adhesive (e.g., pressure-sensitive adhesive). In its "inactive" configuration as shown in FIGS. 24-25, the drug delivery assembly 270 of the patch 200 securely retains a drug compound 207 so that it does not flow to any significant extent into the microneedles 230. When it is desired to "activate" the patch, the release member 210 may be peeled away and removed, such as illustrated in FIGS. 26-27, to break the seal previously formed between the release member 210 and the aperture (not shown) of the support 212. Thereafter, the second section 260 may be folded about a fold line "F" as shown by the directional arrow in FIG. 28 so that the rate control member 208 is positioned vertically adjacent to the support 212 and in fluid communication therewith. Alternatively, the first section 250 may be folded. Regardless, folding of the sections 250 and/or 260 initiates the flow of a drug compound 207 from the drug delivery assembly 270 and into the channels 231 of the microneedles 230 via the support 212 (See FIG. 29).

Other delivery control mechanisms may be utilized in a device. According to one embodiment, a transdermal device may include a housing with microelectronics and other micro-machined structures to control the rate of delivery either according to a preprogrammed schedule or through active interface with the patient, a healthcare professional, or a biosensor. The device may include a material at a surface having a predetermined degradation rate, so as to control release of an agent contained within the device. A delivery rate may be controlled by manipulating a variety of factors, including the characteristics of the formulation to be delivered (e.g., viscosity, electric charge, and/or chemical composition); the dimensions of each device (e.g., outer diameter and the volume of any openings); the number of microneedles on a transdermal patch; the number of individual devices in a carrier matrix; the application of a driving force (e.g., a concentration gradient, a voltage gradient, a pressure gradient); the use of a valve; and so forth.

Transportation of agents through the device may be controlled or monitored using, for example, various combinations of valves, pumps, sensors, actuators, and microprocessors. These components may be produced using standard manufacturing or microfabrication techniques. Actuators that may be useful with the device may include micropumps, microvalves, and positioners. For instance, a microprocessor may be programmed to control a pump or valve, thereby controlling the rate of delivery.

Flow of an agent through the device may be based on diffusion or capillary action, or may be induced using conventional mechanical pumps or nonmechanical driving forces, such as electroosmosis or electrophoresis, or convection. For example, in electroosmosis, electrodes are positioned on a biological surface (e.g., the skin surface), a microneedle, and/or a substrate adjacent a microneedle, to create a convective flow which carries oppositely charged ionic species and/or neutral molecules toward or into the delivery site.

Flow of an agent may be manipulated by selection of the material forming the microneedle surface. For example, one or more large grooves adjacent the microneedle surface of the device may be used to direct the passage of drug, particularly in a liquid state. Alternatively, the physical surface properties of the device may be manipulated to either promote or inhibit transport of material along the surface, such as by controlling hydrophilicity or hydrophobicity.

The flow of an agent may be regulated using valves or gates as is known in the art. Valves may be repeatedly opened and closed, or they may be single-use valves. For example, a breakable barrier or one-way gate may be installed in the device between a reservoir and the patterned surface. When ready to use, the barrier may be broken or gate opened to permit flow through to the microneedle surface. Other valves or gates used in the device may be activated thermally, electrochemically, mechanically, or magnetically to selectively initiate, modulate, or stop the flow of molecules through the device. In one embodiment, flow is controlled by using a rate-limiting membrane as a "valve."

In general, any agent delivery control system, including reservoirs, flow control systems, sensing systems, and so forth as are known in the art may be incorporated with devices. By way of example, U.S. Pat. Nos. 7,250,037, 7,315,758, 7,429,258, 7,582,069, and 7,611,481 describe reservoir and control systems as may be incorporated in devices.

Agents as may be delivered by the device may be intended for the local area near the device or may be intended for wider distribution. For instance, in one embodiment, the device may deliver agents for pain management or inflammation management to a local area around a joint, for instance in treatment of osteoarthritis or rheumatoid arthritis.

The nanotopography of the device may improve delivery of agents while minimizing foreign body and immune response. This may prove particularly beneficial when considering delivery of oligonucleotides and other therapeutics to the nuclear envelope. In the past, delivery of materials (e.g., plasmids, siRNA, RNAi, and so forth), to the nuclear envelope has proven problematic because even when endocytosis is achieved, proper endosomal delivery to the nuclear envelope has proven difficult, most likely due to foreign body and immune response. Once in the cytoplasm, delivered material is often recycled via late endosomes or degraded in the lysosome. By use of disclosed devices, interaction of a microneedle with the ECM may prevent foreign body response within a cell following endocytosis and encourage delivery of the materials to the nucleus.

Delivery of protein therapeutics has likewise proven problematic in the past. For instance, delivery of high molecular weight agents such as protein therapeutics has proven difficult for transdermal delivery routes due to the natural barriers of the skin. The presence of the nanotopography of a microneedle may beneficially affect the thermodynamics of the ECM and improve efficiency of delivery and uptake of protein therapeutics. As utilized herein, the term 'protein therapeutics' generally refers to any biologically active proteinaceous compound including, without limitation, natural, synthetic, and recombinant compounds, fusion proteins, chimeras, and so forth, as well as compounds including the 20 standard amino acids and/or synthetic amino acids. For instance, the presence of the device in or near the stratum granulosum may open tight junctions and allow paracellular transport of high molecular weight agents. In one embodiment, the device may be utilized in transdermal delivery of high molecular weight agents (e.g., agents defining a molecular weight greater than about 400 Da, greater than about 10 kDa, greater than about 20 kDa, or greater than about 100 kDa, e.g., about 150 kDa). Additionally, variation of the surface area to volume ratio of the device may be utilized to alter protein adsorption at the surface of the device, which may in turn alter delivery and cellular uptake of materials. Thus, deliver of a particular material may be optimized through optimization of the surface area/volume ratio of the device.

Even when considering delivery of small molecular weight agents, the device may provide increased efficiency and improved uptake due to interaction of the device with components of the dermal connective tissue and accompanying decrease in foreign body response and improvement in localized chemical potential of the area.

Of course, devices are not limited to targeted delivery of agents. Systemic deliver of agents is also encompassed herein as is withdrawal of an agent from a subject via the device.

There is no particular limitation to agents as may be delivered by use of the device. Agents may include proteinaceous agents such as insulin, immunoglobulins (e.g., IgG, IgM, IgA, IgE), TNF-α, antiviral medications, and so forth; polynucleotide agents including plasmids, siRNA, RNAi, nucleoside anticancer drugs, vaccines, and so forth; and small molecule agents such as alkaloids, glycosides, phenols, and so forth. Agents may include anti-infection agents, hormones, drugs regulating cardiac action or blood flow, pain control, and so forth. Still other substances which may be delivered in accordance with the present disclosure are agents useful in the prevention, diagnosis, alleviation, treatment, or cure of disease. A non-limiting listing of agents includes anti-Angiogenesis agents, anti-depressants, antidiabetic agents, antihistamines, anti-inflammatory agents, butorphanol, calcitonin and analogs, COX-II inhibitors, dermatological agents, dopamine agonists and antagonists, enkephalins and other opioid peptides, epidermal growth factors, erythropoietin and analogs, follicle stimulating hormone, glucagon, growth hormone and analogs (including growth hormone releasing hormone), growth hormone antagonists, heparin, hirudin and hirudin analogs such as hirulog, IgE suppressors and other protein inhibitors, immunosuppressives, insulin, insulinotropin and analogs, interferons, interleukins, leutenizing hormone, leutenizing hormone releasing hormone and analogs, monoclonal or polyclonal antibodies, motion sickness preparations, muscle relaxants, narcotic analgesics, nicotine, non-steroid anti-inflammatory agents, oligosaccharides, parathyroid hormone and analogs, parathyroid hormone antagonists, prostaglandin antagonists, prostaglandins, scopolamine, sedatives, serotonin agonists and antagonists, sexual hypofunction, tissue plasminogen activators, tranquilizers, vaccines with or without carriers/adjuvants, vasodilators, major diagnostics such as tuberculin and other hypersensitivity agents as described in U.S. Pat. No. 6,569,143 entitled "Method of Intradermally Injecting Substances", the entire content of which is incorporated herein by reference. Vaccine formulations may include an antigen or antigenic composition capable of eliciting an immune response against a human pathogen or from other viral pathogens.

In one preferred embodiment, the device may be utilized in treatment of a chronic condition, such as rheumatoid arthritis, to deliver a steady flow of an agent, to a subject in need thereof. RA drugs that may be delivered via disclosed devices may include symptom suppression compounds, such as analgesics and anti-inflammatory drugs including both steroidal and non-steroidal anti-inflammatory drugs (NSAID), as well as disease-modifying antirheumatic drugs (DMARDs).

The device may include and deliver symptom suppression compounds, such as analgesics and anti-inflammatory drugs, as well as DMARD compounds, including biological DMARDs. While not wishing to be bound to any particular theory, it is understood that the nanometer-scale structures fabricated on the surface of the device improve deliver of the compounds across the dermal barrier. Through utilization of the device, RA drugs may be delivered at a steady concentration over a sustained period. The device may prevent the initial burst of concentration common when utilizing previously known methods for delivery of RA drugs, including oral delivery and injection.

The present disclosure may be further understood with reference to the Examples provided below.

EXAMPLE 1

Several different molds were prepared using photolithography techniques similar to those employed in the design and manufacture of electrical circuits. Individual process steps are generally known in the art and have been described. The formed molds may be utilized as a positive mold master for forming a negative mold segment as described herein.

Initially, silicon substrates were prepared by cleaning with acetone, methanol, and isopropyl alcohol, and then coated with a 258 nanometer (nm) layer of silicon dioxide according to a chemical vapor deposition process.

A pattern was then formed on each substrate via an electron beam lithography patterning process as is known in the art using a JEOL JBX-9300FS EBL system. The processing conditions were as follows:

Beam current=11 nA
Acceleration voltage=100 kV
Shot pitch=14 nm
Dose=260 µC/cm$^2$
Resist=ZEP520A, ~330 nm thickness
Developer=n-amyl acetate
Development=2 min. immersion, followed by 30 sec. isopropyl alcohol rinse.

A silicon dioxide etch was then carried out with an STS Advanced Oxide Etch (AOE). Etch time was 50 seconds utilizing 55 standard cubic centimeters per minute (sccm) He, 22 sccm $CF_4$, 20 sccm $C_4F_8$ at 4 mTorr, 400 W coil, 200 W RIE and a DC Bias of 404-411 V.

Following, a silicon etch was carried out with an STS silicon oxide etch (SOE). Etch time was 2 minutes utilizing 20 sccm $Cl_2$ and 5 sccm Ar at 5 mTorr, 600 W coil, 50 W RIE and a DC Bias of 96-102 V. The silicon etch depth was 500 nm.

A buffered oxide etchant (BOE) was used for remaining oxide removal that included a three minute BOE immersion followed by a deionized water rinse.

An Obducat NIL-Eitre®6 nanoimprinter was used to form nanopatterns on a variety of polymer substrates. External water was used as coolant. The UV module utilized a single pulsed lamp at a wave length of between 200 and 1000 nm at 1.8 W/cm$^2$. A UV filter of 250-400 nm was used. The exposure area was 6 inches with a maximum temperature of 200° C. and 80 Bar. The nanoimprinter included a semi-automatic separation unit and automatic controlled demolding.

To facilitate the release of the nanoimprinted films from the molds, the molds were treated with Trideca-(1,1,2,2-tetrahydro)-octytrichlorosilane ($F_{13}$-TCS). To treat a mold, the silicon mold was first cleaned with a wash of acetone, methanol, and isopropyl alcohol and dried with a nitrogen gas. A Petri dish was placed on a hot plate in a nitrogen atmosphere and 1-5 ml of the $F_{13}$-TCS was added to the Petri dish. A silicon mold was placed in the Petri dish and covered for 10-15 minutes to allow the $F_{13}$-TCS vapor to wet out the silicon mold prior to removal of the mold.

Five different polymers as given in Table 1, below, were utilized to form various nanotopography designs.

TABLE 1

| Polymer | Glass Transition Temperature, $T_g$ (K) | Tensile Modulus (MPa) | Surface Tension (mN/m) @20° C. |
|---|---|---|---|
| Polyethylene | 140-170 | 100-300 | 30 |
| Polypropylene | 280 | 1,389 | 21 |
| PMMA | 322 | 3,100 | 41 |
| Polystyrene | 373 | 3,300 | 40 |
| Polycarbonate | 423 | 2,340 | 43 |

Several different nanotopography patterns were formed, schematic representations of which are illustrated in FIGS. 30A-30D. The nanotopography pattern illustrated in FIG. 30E was a surface of a flat substrate purchased from NTT Advanced Technology of Tokyo, Japan. The patterns were designated DN1 (FIG. 30A), DN2 (FIG. 30B), DN3 (FIG. 30C), DN4 (FIG. 30D) and NTTAT2 (FIG. 30E). SEM images of the molds are shown in FIGS. 30A, 30B, and 30C, and images of the films are shown in FIGS. 30D and 30E. FIG. 15 illustrates a nanopatterned film formed by use of the mold of FIG. 30A (DN1). In this particular film, the polymer features were drawn by temperature variation as previously discussed. The surface roughness of the pattern of FIG. 30E was found to be 34 nm.

The pattern illustrated in FIGS. 14C and 14D was also formed according to this nanoimprinting process. This pattern included the pillars 72 and pillars 62, as illustrated. Larger pillars 72 were formed with a 3.5 micrometer (µm) diameter and 30 µm heights with center-to-center spacing of 6.8 µm. Pillars 62 were 500 nm in height and 200 nm in diameter and a center-to-center spacing of 250 nm.

The nanoimprinting process conditions used with polypropylene films are provided below in Table 2.

TABLE 2

| Time (s) | Temperature (C.) | Pressure (Bar) |
|---|---|---|
| 10 | 50 | 10 |
| 10 | 75 | 20 |
| 10 | 100 | 30 |
| 420 | 160 | 40 |
| 180 | 100 | 40 |
| 180 | 50 | 40 |
| 180 | 25 | 40 |

EXAMPLE 2

Films were formed as described above in Example 1 including various different patterns and formed of either polystyrene (PS) or polypropylene (PP). The patterns are representative of patterns that may be incorporated on the microneedle segment of a mold segment as described herein.

Patterns utilized were DN2, DN3, or DN4 utilizing formation processes as described in Example 1. The underlying substrate varied in thickness. The pattern molds were varied with regard to hole depth and feature spacing to form a variety of differently-sized features having the designated patterns. Sample no. 8 (designated BB1) was formed by use of a 0.6 µm millipore polycarbonate filter as a mold. A 25 µm polypropylene film was laid over the top of the filter and was then heated to melt such that the polypropylene could flow into the pores of the filter. The mold was then cooled and the polycarbonate mold dissolved by use of a methylene chloride solvent.

SEMs of the formed films are shown in FIGS. 31-39 and the characteristics of the formed films are summarized in Table 3, below.

The fractal dimension may also be evaluated from 2D Fourier spectra by application of the Log Log function. If the surface is fractal the Log Log graph should be highly linear, with at negative slope (see, e.g., Fractal Surfaces, John C. Russ, Springer-Verlag New York, LLC, July, 2008).

While the subject matter has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present disclosure should be assessed as that of the appended claims and any equivalents thereto.

What is claimed is:

1. An injection molded microneedle array comprising:
    a substrate;

TABLE 3

| Sample No. | FIG. | Pattern | Material | Film thickness (µm) | Pattern Feature[1] | Cross Sectional Dimension[2] | Feature height[3] | Aspect Ratio | Surface Roughness (nm) | Fractal Dimension | Water Contact Angle |
|---|---|---|---|---|---|---|---|---|---|---|---|
| 1 | 31 | DN3 | PS | 75 | A | 1100 nm | 520 nm | 0.47 | 150 | 2.0 | 100° |
|   |   |   |   |   | B | 400 nm | 560 nm | 1.4 |   |   |   |
|   |   |   |   |   | C | 200 nm | 680 nm | 3.4 |   |   |   |
| 2 | 32A, 32B | DN2 | PP | 5.0 | n/a | 200 nm | 100 nm | 0.5 | 16 | 2.15 | 91° |
| 3 | 33 | DN2 | PS | 75 | n/a | 200 nm | 1.0 µm | 5 | 64 | 2.2 | 110° |
| 4 | 34 | DN2 | PP | 25.4 | n/a | 200 nm | 300 nm | 1.5 | 38 | 1.94 | 118° |
| 5 | 35 | DN3 | PS | 75 | A | 1100 nm | 570 nm | 0.52 | 21.1 | 1.98 | 100° |
|   |   |   |   |   | B | 400 nm | 635 nm | 1.6 |   |   |   |
|   |   |   |   |   | C | 200 nm | — | — |   |   |   |
| 6 | 36 | DN4 | PS | 75 | n/a | 200 nm | — | — | 30.6 | 2.04 | 80° |
| 7 | 37 | DN4 | PP | 25.4 | n/a | 200 nm | — | — | 21.4 | 2.07 | 112° |
| 8 | 38 | BB1 | PP | 25.4 | n/a | 600 nm | 18 µm | 30 | 820 | 2.17 | 110° |
| 9 | 39 | DN3 | PP | 5 | A | 1100 nm | 165 nm | 0.15 | 50 | 2.13 |   |
|   |   |   |   |   | B | 400 nm | 80 nm | 0.2 |   |   |   |
|   |   |   |   |   | C | 200 nm | 34 nm | 0.17 |   |   |   |

[1]Pattern Features as shown on the figures.
[2]Cross sectional dimension values were derived from the mold and equated as an approximation of the maximum dimension of the structure, although it should be understood that the actual dimension of any given individual structure may vary slightly as may be seen in the figures.
[3]Feature heights are provided as the average of several individually determined feature heights For each sample AFM was utilized to characterize the film. Characterizations included formation of scanning electron micrograph (SEM), determination of surface roughness, determination of maximum measured feature height, and determination of fractal dimension.

The atomic force microscopy (AFM) probe utilized was a series 16 silicon probe and cantilever available from µMasch. The cantilever had a resonant frequency of 170 kHz, a spring constant of 40 N/m, a length of 230±5 µm, a width of 40±3 µm, and a thickness of 7.0±0.5 µm. The probe tip was an n-type phosphorous-doped silicon probe, with a typical probe tip radius of 10 nm, a full tip cone angle of 40°, a total tip height of 20-25 µm, and a bulk resistivity 0.01-0.05 ohm-cm.

The surface roughness value given in Table 3 is the arithmetical mean height of the surface (Sa) areal roughness parameter as defined in the ISO 25178 series.

The Fractal Dimension was calculated for the different angles by analyzing the Fourier amplitude spectrum; for different angles the amplitude Fourier profile was extracted and the logarithm of the frequency and amplitude coordinates calculated. The fractal dimension, D, for each direction is then calculated as $$D=(6+s)/2,$$

where s is the (negative) slope of the log-log curves. The reported fractal dimension is the average for all directions.

a plurality of microneedles extending from a surface of the substrate;
a plurality of nanostructures and microstructures on a surface and projecting directly outward therefrom of at least one of the microneedles in a predetermined pattern,
wherein at least a portion of the microstructures have a cross-sectional dimension of greater than about 500 nanometers and less than about 10 micrometers and a height of from about 20 nanometers to about 1 micrometer, and, wherein at least a portion of the nanostructures have a cross-sectional dimension of less than about 500 nanometers and greater than about 5 nanometers, wherein at least one of the microneedies defines a channel; and
wherein the substrate, the pluraiity of microneedles and the plurality of nanostructures are all portions of an injection molded construct.

2. The injection molded microneedle array of claim 1, further comprising second nanostructures having a cross-sectional dimension less than the cross-sectional dimension of the microstructures and greater than the cross-sectional dimension of the plurality of nanostructures.

3. A transdermal patch comprising the injection molded microneedle array of claim 1.

4. The transdermal patch of claim 3, further comprising a reservoir for holding a drug compound.

5. The transdermal patch of claim 4, further comprising a rate control membrane in fluid communication with the reservoir.

6. The transdermal patch of claim 5, further comprising a release member that is generally impermeable to the drug compound and positioned adjacent to the rate control membrane.

7. The transdermal patch of claim 3, wherein the drug compound has a molecular weight between about 20 kDa and about 250 kDa.

8. The injection molded microneedle array of claim 1, wherein at least a portion of the nanostructures have a center-to-center spacing of from about 50 nanometers to about 1 micrometer.

9. The injection molded microneedle array of claim 1, wherein at least a portion of the nanostructures have a height of from about 10 nanometers to about 1 micrometer.

10. The injection molded microneedle array of claim 1, wherein at least a portion of the nanostructures have an aspect ratio of from about 0.2 to about 5.

11. The injection molded microneedle array of claim 1, wherein the pattern has a fractal dimension of greater than about 1.

12. The injection molded microneedle array of claim 1, wherein at least a portion of the nanostructures have a cross-sectional dimension of from about 100 to about 300 nanometers.

13. The injection molded microneedle array of claim 1, wherein the nanostructures have approximately the same cross-sectional dimension.

14. The injection molded microneedle array of claim 1, wherein the ratio of the cross sectional dimension of two adjacent nanostructures to the center-to-center spacing between those two structures is between about 1:1 and about 1:4.

15. The injection molded microneedle array of claim 1, wherein at least a portion of the nanostructures have an equidistant spacing.

16. The injection molded microneedle array of claim 1, wherein the channel has a cross-sectional dimension of from about 1 to about 100 micrometers.

17. The injection molded microneedle array of claim 16, wherein the channel has a length of from about 10 to about 800 micrometers.

18. The injection molded microneedle array of claim 1, wherein the array contains a base having an aperture, wherein the aperture is in at least partial alignment with the channel of a microneedle.

19. The injection molded microneedle array of claim 4, wherein the reservoir is removably connected to the array.

20. The injection molded microneedle array of claim 1, wherein the nanostructures are in the form of pillars.

21. The injection molded microneedle array of claim 1, wherein at least a portion of the nanostructures have an aspect ratio of from about 0.5 to about 3.5.

22. The injection molded microneedle array of claim 1, wherein at least a portion of the nanostructures have a cross-sectional dimension of from about 20 to about 400 nanometers and at least a portion of the microstructures have a cross-sectional dimension of from about 600 nanometers to about 1.5 micrometers.

23. The injection molded microneedle array of claim 1, wherein at least a portion of the microstructures have an aspect ratio of from about 0.2 to about 5.

24. The injection molded microneedle array of claim 1, wherein the cross-sectional dimension of the microstructures is greater than the height of the microstructures.

25. The injection molded microneedle array of claim 24, wherein at least a portion of the microstructures have an aspect ratio of from about 0.15 to 1.

26. The injection molded microneedle array of claim 1, wherein at least a portion of the nanostructures have a height greater than a cross-sectional dimension.

* * * * *